US010241076B2

(12) United States Patent
Patolsky et al.

(10) Patent No.: US 10,241,076 B2
(45) Date of Patent: Mar. 26, 2019

(54) SYSTEMS AND METHODS FOR IDENTIFYING EXPLOSIVES

(71) Applicant: Tracense Systems Ltd., Herzlia (IL)

(72) Inventors: Fernando Patolsky, Rechovot (IL); Ronen Shacham, Nes Ziona (IL); Amir Lichtenstein, Tel-Aviv (IL); Ehud Havivi, Natania (IL); Ehud Hahamy, Modiln (IL)

(73) Assignee: Tracense System Ltd., Herzlia (IL)

( * ) Notice: Subject to any disclaimer, the term of this patent is extended or adjusted under 35 U.S.C. 154(b) by 553 days.

(21) Appl. No.: 14/762,001

(22) PCT Filed: Jan. 20, 2014

(86) PCT No.: PCT/IL2014/050070
§ 371 (c)(1),
(2) Date: Jul. 20, 2015

(87) PCT Pub. No.: WO2014/111944
PCT Pub. Date: Jul. 24, 2014

(65) Prior Publication Data
US 2015/0316523 A1 Nov. 5, 2015

Related U.S. Application Data

(60) Provisional application No. 61/754,593, filed on Jan. 20, 2013.

(51) Int. Cl.
*G01N 33/22* (2006.01)
*G01N 33/00* (2006.01)
(Continued)

(52) U.S. Cl.
CPC ......... *G01N 27/4146* (2013.01); *C40B 30/02* (2013.01); *G01N 33/0031* (2013.01);
(Continued)

(58) Field of Classification Search
CPC ................ C40B 30/02; G01N 27/4146; G01N 33/0031; G01N 33/0036; G01N 33/0037;
(Continued)

(56) References Cited

U.S. PATENT DOCUMENTS 7,619,290 B2  11/2009  Lieber et al.
8,178,357 B2   5/2012  Trogler et al.
(Continued)

FOREIGN PATENT DOCUMENTS

WO  WO 2011/154939  12/2011
WO  WO 2013/095730   6/2013
WO  WO 2014/111944   7/2014

OTHER PUBLICATIONS

International Preliminary Report on Patentability dated Jul. 30, 2015 From the International Bureau of WIPO Re. Application No. PCT/IL2014/050070.
(Continued)

*Primary Examiner* — Maureen Wallenhorst

(57) ABSTRACT

In a method for identifying an explosive in a sample, an explosive fingerprint defined by a set of kinetic parameters is received. The kinetic parameters describe a plurality of interactions between the explosive and each of a respective plurality of functional moieties. A data processor is used for accessing a database of explosive fingerprints, and searching the database for a database fingerprint matching the received fingerprint.

24 Claims, 26 Drawing Sheets
(12 of 26 Drawing Sheet(s) Filed in Color)

(51) Int. Cl.
 G01N 27/414 (2006.01)
 C40B 30/02 (2006.01)
 H01L 29/772 (2006.01)
(52) U.S. Cl.
 CPC ....... *G01N 33/0057* (2013.01); *G01N 33/227* (2013.01); *H01L 29/772* (2013.01)
(58) Field of Classification Search
 CPC .............. G01N 33/0057; G01N 33/227; Y10T 436/17; Y10T 436/170769; Y10T 436/173845; Y10T 436/206664; Y10T 436/25875; H01L 29/772
 USPC ......... 436/72, 106, 107, 111, 135, 149, 151, 436/181; 422/82.01, 82.02, 88, 90; 506/2, 8, 15, 22
 See application file for complete search history.

(56) References Cited

U.S. PATENT DOCUMENTS

| | | | |
|---|---|---|---|
| 2008/0116490 A1 | 5/2008 | Stewart et al. | |
| 2009/0275143 A1* | 11/2009 | Misra | G01N 27/127 436/130 |
| 2010/0022012 A1 | 1/2010 | Lieber et al. | |
| 2010/0129925 A1* | 5/2010 | Afzali-Ardakani | B82Y 10/00 436/151 |
| 2010/0325073 A1 | 12/2010 | Haick | |
| 2011/0151574 A1* | 6/2011 | Chen | B82Y 30/00 436/149 |

OTHER PUBLICATIONS

International Search Report and the Written Opinion dated May 15, 2014 From the International Searching Authority Re. Application No. PCT/IL2014/050070.
Cho et al. "Recognition of Explosive Precursors Using Nanowire Sensor Array and Decision Tree Learning", IEEE Sensors Journal, 12(7): 2384-2391, Jul. 2012.
Clavaguera et al. "Sub-PPM Detection of Nerve Agents Using Chemically Functionalized Silicon Nanoribbon Field-Effect Transistors", Angewandte Chemie International Edition, 49: 4063-4066, 2010.
Cui et al. "Nanowire Nanosensors for Highly Sensitive and Selective Detection of Biological and Chemical Species", Science, 293: 1298-1292, 2001.
Dobrokhotov et al. "ZnO Coated Nanospring-Based Chemiresistors", Journal of Applied Physics, 111: 044311-1-044311-8, Feb. 23, 2012.
Dubnikova et al. "Novel Approach to the Detection of Triacetone Triperoxide (TATP): Its Structure and Its Complexes With Ions", The Journal of Physical Chemistry A, 106(19): 4951-4956, Apr. 18, 2002.
Engel et al. "Supersensitive Detection of Explosives by Silicon Nanowire Arrays", Angewandte Chemie International Edition, 49(38): 6830-6835, 2010.
Li et al. "Sequence-Specific Label-Free DNA Sensors Based on Silicon Nanowires", Nano Letters, 4(2): 245-247, 2004.
Llobet et al. "Qualitative and Quantitative Analysis of Volatile Organic Compounds Using Transient and Steady-State Responses of a Thick-Film Tin Oxide Gas Sensor Array", Sensor and Actuators B: Chemical, 41(1-3): 13-21, Jun. 30, 1997. Abstract, Section 2. Experimental.
McAlpine et al. "Highly Ordered Nanowire Arrays on Plastic Substrates for Ultrasensitive Flexible Chemical Sensors", Nature Materials, 6: 379-384, May 2007.
McAlpine et al. "Peptide-Nanowire Hybrid Materials for Selective Sensing of Small Molecules", Journal of the American Chemical Society, JACS, 130(20): 9583-9589, Jul. 2008.
Nair et al. "Performance Limits of Nanobiosensors", Applied Physics Letters, 88: 233120-1-233120-3, 2006.
Patolsky et al. "Electrical Detection of Single Viruses", Proc. Natl. Acad. Sci. USA, PNAS, 101(39): 14017-14022, Sep. 28, 2004.
Patolsky et al. "Nanowire-Based Biosensors", Analytical Chemistry, 78: 4260-4269, Jul. 1, 2006.
Stern et al. "Semiconducting Nanowire Field-Effect Transistor Biomolecular Sensors", IEEE Transactions on Electron devices, 55(11): 3119-3130, Nov. 2008.
Terrier "Rate and Equilibrium Studies in Jackson-Meisenheimer Complexes", Chemical Reviews, 82(2): 78-152, Apr. 1982.
Timko et al. "Electrical Recording From Hearts With Flexible Nanowire Device Arrays", Nano Letters, 9(2):914-918, Feb. 2009.
Zheng et al. "Multiplexed Electrical Detection of Cancer Markers With Nanowire Sensor Arrays", Nature Biotechnology, 23(10): 1294-1301, Oct. 2005.
Supplementary European Search Report and the European Search Opinion dated Jul. 25, 2016 From the European Patent Office Re. Application No. 14740177.2.
Dobrokhotov et al. "Toward the Nanospring-Based Artificial Olfactory System for Trace-Detection of Flammable and Explosive Vapors", Sensors and Actuators B: Chemical, XP028508990, 168: 138-148, Available Online Apr. 6, 2012. Abstract, p. 138, col. 2, Lines 21-23, Fig.4, p. 141, col. 2, Lines 4-13, p. 143, col. 1, Lines 11-23, p. 146, col. 1, Lines 14-20.
Sljukic et al. "Iron Oxide Particles Are the Active Sites for Hydrogen Peroxide Sensing at Multiwalled Carbon Nanotube Modified Electrodes", Nano Letters, XP055005714, 6(7): 1556-1558, Published on Web Jun. 29, 2006.

\* cited by examiner

Aminopropyltriethoxysilane

N-(2-aminoethyl)-3-aminopropyltrimethoxysilane 4-amino-3,3-dimethyl butyl triethoxysilane Trinitrotoluene RDX (Cyclotrimethylenetrinitramine)

Octahydro-1,3,5,7-tetranitro-1,3,5,7-tetrazocine (HMX)

Pentaerythritol tetranitrate (PETN)

NG (1- Nitroglycerin)

Statistical fingerprint

Matching to threats library

SYSTEMS AND METHODS FOR IDENTIFYING EXPLOSIVES

RELATED APPLICATIONS

This application is a National Phase of PCT Patent Application No. PCT/IL2014/050070 having International filing date of Jan. 20, 2014, which claims the benefit of priority under 35 USC § 119(e) of U.S. Provisional Patent Application No. 61/754,593 filed on Jan. 20, 2013. The contents of the above applications are all incorporated by reference as if fully set forth herein in their entirety.

FIELD AND BACKGROUND OF THE INVENTION

The present invention, in some embodiments thereof, relates to detection of chemicals and, more particularly, but not exclusively, to devices, systems and methods useful for detecting and identifying explosives.

An 'explosive' is a highly energetic, chemically-unstable molecule having a rapid rate of autodecomposition, typically with the accompanying evolution of large amounts of heat and gaseous products. There has been a great increase in the development of low trace and ultra-low trace explosive detection in the last decade, mainly due to the globalization of terrorist acts, clearing of old mine fields, and the reclamation of contaminated land previously used for military purposes.

In addition, the availability of raw materials for the preparation of explosives, together with the growing access to information on preparing these explosives, allows for almost anyone with sufficient will and internet access to prepare an explosive device, known as improvised explosives devices or IED's. The vast number of people passing through borders, public places, airports etc. poses a huge challenge for current day security screening technologies. The same challenge applies to home, and building and critical infrastructure security. The ultimate goal is of course to be able to rapidly and effectively screen every passing person and his belongings, without the need to delay the traffic of people, and without human contact if possible.

Explosives, especially concealed ones, have a very low vapor pressure or 'signature' in the surrounding air. The effective vapor pressure of explosives can be reduced by terrorists by a factor of up to 1000, with the use of plastic packages. Detection methods for traces of explosives therefore continue to be plagued by the low volatility of many target analytes.

One of the most commonly-used high explosives over the last 100 years is 2,4,6-trinitrotoluene (TNT), which poses not only a direct security threat, but also great environmental concern due to soil and water contamination near production, storage and test sites.

Analytical procedures in use today for the trace detection of explosives typically involve collecting vapor samples and analyzing them with a sensitive method. Several methodologies have been reported for detecting TNT and other nitro-containing explosives. These are based on electro-chemistry, ion-mobility spectrometry, gas chromatography, HPLC, photoluminescence, surface acoustic-wave devices, microcantilevers, fluorescent polymers, surface plasmon resonance, quartz crystal microbalance, immunosensors and other methods. In these existing methods, pre-concentration of air or liquid samples is usually required for a measurable signal to be recorded by the sensor. These procedures are time-consuming, and delay the operation of a sensor. Although some reported methods are very sensitive and selective, most are rather expensive, time-consuming and require bulky equipment, tedious sample preparation and an expert operator. Furthermore, these systems cannot be miniaturized and automated or cannot perform high-throughput analysis.

Table 1 below presents data comparing TNT detection by various currently-employed methodologies.

TABLE 1

| Detection Method | Detection Limit |
|---|---|
| remote microelectrode electrochemical sensor in water | 50 ppb |
| luminescent oligo(tetraphenyl)silole nanoparticles in water | 20 ppb |
| quenching of fluorescence of polymer films in air | 10 ppb |
| electrochemical detection by carbon nanotubes in water | 5 ppb |
| biochip (on Au) via QCM or SPR in water | 1-10 ppb |
| electrochemical detection using metallic NP-CNT composites in water | 1 ppb |
| adsorptive stripping by carbon nanotubes-modified GCE in water | 600 ppt |
| electrochemical detection by mesoporous SiO2-modified electrodes in water | 414 ppt |
| oligo(ethylene glycol)-based SPR in water | 80 ppt |
| electrochemical sensing by imprinted electro-polymerized bis-aniline-cross-linked AuNPs in water | 46 ppt |
| SPR, fabricated dinitrophenylated-keyhole lympet hemocyanin (DNP-KLH) protein conjugate (in water) | 5 ppt |
| indirect competitive immunoassay using SPR (in water) | 2 ppt |
| SPR sensing by bis-aniline-cross-linked picric acid-imprinted Au-nanoparticles composite in water | $1.2 \times 10^{-3}$ ppt |
| IMS (ion mobility spectroscopy) from air and water samples | 5-10 ppt |
| SAW in water | 10 ppt |
| conducting polymers in water | 20-40 ppt |
| µ-Electron capture detector | 100 ppt |
| Airport sniffers from air samples | 2000 ppt |

Specially-trained dogs can detect explosives with the use of their noses which are very sensitive to scents. These dogs are trained by expert handlers to identify the scents of several common explosive materials and notify the handler when they detect one of these scents. While being very effective, the usefulness of such dogs becomes easily degraded when a dog becomes tired or bored, thus limiting their range of application.

Peroxides-based explosives (e.g., cyclic organic peroxides) have also been used recently to build improvised explosive devices, increasing worldwide the awareness thereto. Development of methodologies for the detection of triacetone triperoxide (TATP), hexamethylene triperoxide diamine (HMTD), tetramethylene diperoxide dicarbamide (TMDD) and other cyclic organic peroxides have become an urgent priority. Most organic peroxides are explosive, and some compounds can be easily synthesized by mixing common commercial products such as acetone, hydrogen peroxide and strong acids. Most of the current technology in use for trace detection of explosives is unable to detect peroxide-based explosives [Oxley et al. *Propellants, Explosives, Pyrotechnics* 34, 539-543 (2009); Önnerud, H., Wallin, S. & Östmark, H. in *Intelligence and Security Informatics Conference (EISIC)*, 2011 European. 238-243 (IEEE)].

Past theoretical studies have showed a plausible approach based on the formation of complexes between the molecular ring structures of cyclic organic peroxide explosives and a central metal moiety, analogous to the formation of clathrates and crown ethers that selectively bind to ionic species in solution. These studies have predicted that TATP molecules can bind to several ions of different valency, with $In^{3+}$, $Zn^{2+}$ and $Ti^{4+}$ showing the highest binding energy [Dubnikova, F., Kosloff, R., Zeiri, Y. & Karpas, Z. *The Journal of Physical Chemistry A* 106, 4951-4956 (2002)].

Semiconducting nanowires are known to be extremely sensitive to chemical species adsorbed on their surfaces. For a nanowire device, the binding of a charged analyte to the surface of the nanowire leads to a conductance change, or a change in current flowing through the wires. The 1D (one dimensional) nanoscale morphology and the extremely high surface-to-volume ratio make this conductance change to be much greater for nanowire-based sensors versus planar FETs (field-effect transistors), significantly increasing the sensitivity is possible.

Nanowire-based field-effect transistors (NW-FETs) have therefore been recognized in the past decade as powerful potential new sensors for the detection of chemical and biological species. See, for example, Patolsky et al., Analytical Chemistry 78, 4260-4269 (2006); Stern et al., IEEE Transactions on Electron Devices 55, 3119-3130 (2008); Cui et al., Science 293, 1289-1292 (2001); Patolsky et al. Proceedings of the National Academy of Sciences of the United States of America 101, 14017-14022 (2004), all being incorporated by reference as if fully set forth herein.

Recently, extensive work has been carried out with the use of nanowire electrical devices for the simultaneous multiplexed detection of multiple biomolecular species of medical diagnostic relevance, such as DNA and proteins [Zheng et al., Nature Biotechnology 23, 1294-1301 (2005); Timko et al., Nano Lett. 9, 914-918 (2009); Li et al., Nano Lett. 4, 245-247 (2004)].

Generally, in a NW-FET configuration, the gate potential controls the channel conductance for a given source drain voltage (VSD), and modulation of the gate voltage (VGD) changes the measured source-drain current (ISD). For NW sensors operated as FETs, the sensing mechanism is the field-gating effect of charged molecules on the carrier conduction inside the NW. Compared to devices made of micro-sized materials or bulk materials, the enhanced sensitivity of nanodevices is closely related to the reduced dimensions and larger surface/volume ratio. Since most of the biological analyte molecules have intrinsic charges, binding on the nanowire surface can serve as a molecular gate on the semiconducting SiNW [Cui et al., 2001, supra].

U.S. Pat. No. 7,619,290, U.S. Patent Application having publication No. 2010/0022012, and corresponding applications, teach nanoscale devices composed of, inter alia, functionalized nanowires, which can be used as sensors.

Recently, Clavaguera et al. disclosed a method for sub-ppm detection of nerve agents using chemically functionalized silicon nanoribbon field-effect transistors [Clavaguera et al., *Angew. Chem. Int. Ed.* 2010, 49, 1-5]. McAlpine et al. [*J. Am. Chem. Soc.* 2008 Jul. 23; 130(29):9583-9] disclosed a scalable and parallel process for transferring hundreds of pre-aligned silicon nanowires onto plastic to yield highly ordered films for low-power sensor chips. The nanowires exhibit parts-per-billion sensitivity to $NO_2$. $SiO_2$ surface chemistries were used to construct a 'nano-electronic nose' library, which can distinguish acetone and hexane vapors via distributed responses [*Nature Materials* Vol. 6, 2007, pp. 379-384].

WO 2011/154939 discloses SiNW-FET devices, chemically-modified with a monolayer of an amine-functionalized silane derivative, which can be efficiently used to detect small amounts of nitro-containing explosives.

Additional background art includes U.S. Patent Application having Publication No. 2010/0325073.

SUMMARY OF THE INVENTION

The present inventors have now devised and successfully prepared and practiced nanostructure arrays, which can be efficiently used for identifying an explosive in a sample.

According to an aspect of some embodiments of the present invention there is provided a system for identifying an explosive. The system comprises a substrate carrying a plurality of sensing devices, each sensing device comprising at least one semiconductor nanostructure having attached thereto a functional moiety selected to interact with an explosive-containing sample. Each sensing device is configured to generate a detectable signal responsively to the interaction, wherein at least two different sensing devices comprise different functional moieties. The system also comprises a signal processor having a circuit configured to extract, from each generated signal, a kinetic parameter describing a respective interaction of the sample with a respective sensing device, thereby to construct an explosive fingerprint indicative of the explosive. The explosive fingerprint is defined as a set of kinetic parameters, at least one parameter for each sensing device.

According to some embodiments of the invention the system comprises a data processor configured to access a database of explosive fingerprints, and to search the database for a database fingerprint matching the constructed fingerprint.

According to some embodiments of the invention at least one of the sensing devices comprises a plurality of semiconductor nanostructures, and is configured to regenerate a group of signals, wherein the signal processor is configured to extract the kinetic parameter collectively from the group of signals.

According to some embodiments of the invention the signal processor is configured to extract pairs of parameters from each signal of the group of signals, thereby to provide a plurality of pairs of parameters, and to calculate the kinetic parameter by fitting the plurality of pairs of parameters to a predetermined fitting function.

According to some embodiments of the invention the signal processor is configure to extract at least one additional parameter from at least one of the signals, and to construct the explosive fingerprint based on the kinetic parameter and based on the at least one additional parameter.

According to some embodiments of the invention the at least one additional parameter describes a plateau segment of the at least one signal.

According to some embodiments of the invention at least one kinetic parameter is extracted from a conductance curve of a respective nanostructure as a function of the time.

According to some embodiments of the invention a functional moiety in at least one of the sensing devices is a moiety which forms a complex with the explosive.

According to some embodiments of the invention a functional moiety in each of the sensing devices is independently a moiety which forms a complex with the explosive.

According to some embodiments of the invention a functional moiety in at least one of the sensing devices is independently a moiety that interacts with a nitro-containing explosive by forming a charge transfer complex.

According to some embodiments of the invention the functional moiety in at least one of the sensing devices is independently an electron donating moiety.

According to some embodiments of the invention a length of the functional moiety in at least one of the sensing devices is smaller than 2 nm.

According to some embodiments of the invention the functional moiety in at least one of the sensing devices is independently selected from the group consisting of C1-10 alkyl, C1-10 alkenyl, aryl and cycloalkyl, each being substituted by an electron donating group.

According to some embodiments of the invention the functional moiety in at least one of the sensing devices is independently selected from the group consisting of a heteroalicyclic and a heteroaryl, each comprising a heteroatom that functions as an electron donating group.

According to some embodiments of the invention the electron donating group is selected from the group consisting of amine, thiol, pyrrole, alkoxy, thioalkoxy, aryloxy and thioaryloxy.

According to some embodiments of the invention the electron donating group is amine.

According to some embodiments of the invention the functional moiety in at least one of the sensing devices is independently selected from the group consisting of aminopropyl, N-(2-aminoethyl)-3-aminopropyl, 4-amino-3,3-dimethyl butyl, p-aminophenyl, and m-aminophenyl.

According to some embodiments of the invention a functional moiety in at least one of the sensing devices is independently a moiety that interacts with a peroxide-containing explosive.

According to some embodiments of the invention the functional moiety that interacts with the peroxide-containing explosive is independently a moiety that comprises particles of a metal oxide.

According to some embodiments of the invention the metal oxide is selected from the group consisting of zinc oxide, titanium dioxide, lithium oxide, copper oxide, an oxide of indium, and an oxide of cadmium.

According to some embodiments of the invention a functional moiety in at least one of the sensing devices is independently the functional moiety that interacts with a nitro-containing explosive by forming a charge transfer complex, and a functional moiety is at least another one of the sensing devices is independently the functional moiety that comprises particles of a metal oxide.

According to some embodiments of the invention the plurality of nanostructures comprises nanowires.

According to some embodiments of the invention the semiconductor nanostructure comprises silicon.

According to some embodiments of the invention the device further comprises a detector constructed and arranged to determine each of the changes in the electrical property of at least one nanostructure.

According to some embodiments of the invention the device comprises or is part of a transistor.

According to an aspect of some embodiments of the present invention there is provided a method of identifying an explosive in a sample, the method comprising contacting the sample with the system as delineated above and optionally as further exemplified below, and analyzing the generated signals to identify the explosive in the sample.

According to an aspect of some embodiments of the present invention there is provided a method of identifying an explosive in a sample. The method comprises receiving an explosive fingerprint defined by a set of kinetic parameters, describing a plurality of interactions between the explosive and each of a respective plurality of functional moieties. The method further comprises using a data processor for accessing a database of explosive fingerprints, and searching the database for a database fingerprint matching the received fingerprint.

According to some embodiments of the invention the method comprises extracting pairs of parameters from each signal of the group of signals, thereby to provide a plurality of pairs of parameters, and calculating the kinetic parameter by fitting the plurality of pairs of parameters to a predetermined fitting function.

According to some embodiments of the invention the system at least one pair of parameters comprises a first parameter describing rise of a respective signal of the group of signals and a second parameter describing a descent of the respective signal.

According to some embodiments of the invention the fitting function is a linear function characterized by a slope, and wherein the kinetic parameter is the slope.

According to some embodiments of the invention the method comprises extracting at least one additional parameter from at least one of the signals, and constructing the explosive fingerprint based on the kinetic parameter and based on the at least one additional parameter.

According to some embodiments of the invention the at least one additional parameter describes a plateau segment of the at least one signal.

According to some embodiments of the invention the explosive is a nitro-containing explosive.

According to some embodiments of the invention the explosive is selected from the group consisting of 2-nitrotoluene; 3-nitrotoluene; 4-nitrotoluene; 2,4,6-trinitrotoluene (TNT); 2,4-dinitrotoluene; 3,4-dinitrotoluene; 2,6-dinitrotoluene; ethylene glycol dinitrate (EGDN); nitroglycerine (NG); cyclotrimethylenetrinitramine (cyclonite; RDX); pentaerythritol tetranitrate (PETN); homocyclonite (octogen; HMX); ammonium nitrate; 1,2,3-propanetrial trinitrate Formulation; and any mixture thereof.

According to some embodiments of the invention the explosive is a peroxide-containing explosive.

According to some embodiments of the invention the system or method wherein the explosive is selected from the group consisting of Triacetone trioxide (TATP) and hexamethylene triperoxide diamine (HMDT).

According to some embodiments of the invention the sample is a fluid sample.

According to some embodiments of the invention the sample is air.

According to some embodiments of the invention the sample is a particle.

According to some embodiments of the invention the sample is a powder.

According to some embodiments of the invention the explosive is in a fluid state.

According to some embodiments of the invention the explosive is in a gaseous state.

According to some embodiments of the invention the explosive is in a solid state.

According to some embodiments of the invention a detectable concentration of the explosive in the sample is lower than 1 micromolar, or lower than 1 nanomolar, or lower than 1 picomolar or lower than 1 femtomolar, e.g., on the order of 1 attomolar.

According to some embodiments of the invention the system or method wherein a detectable concentration of the explosive in the sample ranges from about 1 attomolar to about 1 micromolar.

According to an aspect of some embodiments of the present invention there is provided a system, which comprises a substrate and a semiconductor nanostructure deposited onto the substrate. The nanostructure has a functional moiety associated therewith, the functional moiety being such that upon contacting a peroxide-containing explosive with the system, the nanostructure exhibits a detectable change in an electrical property of the nanostructure.

According to some embodiments of the invention the electrical property is electrical conductance.

According to an aspect of some embodiments of the present invention there is provided a method of determining a presence of a peroxide-containing explosive in a sample. The method comprises contacting the sample with the system as described above, and determining the change in the electrical property.

According to some embodiments of the invention the functional moiety comprises particles of a metal oxide.

According to some embodiments of the invention the particles of metal oxide are attached to the nanostructure by atomic layer deposition.

According to an aspect of some embodiments of the present invention there is provided a process of generating particles of a metal oxide on a nanostructure. The process comprises subjecting a metal or an organometallic complex of the metal to atomic layer deposition in the presence of an oxygen source.

According to an aspect of some embodiments of the present invention there is provided a system for identifying an explosive. The system comprises a substrate carrying a plurality of sensing devices. Each sensing device comprises at least one nanostructure having attached thereto a functional moiety selected to interact with an explosive-containing sample, and is configured to generate a detectable signal responsively to the reaction. In various exemplary embodiments of the invention the plurality of sensing devices comprise at least four sensing devices, wherein different sensing devices comprises different functional moieties, and wherein a plurality of signals respectively generated by the plurality of sensing devices is indicative of the identity of the explosive.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system.

In an exemplary embodiment of the invention, one or more tasks according to exemplary embodiments of method and/or system as described herein are performed by a data processor, such as a computing platform for executing a plurality of instructions.

Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
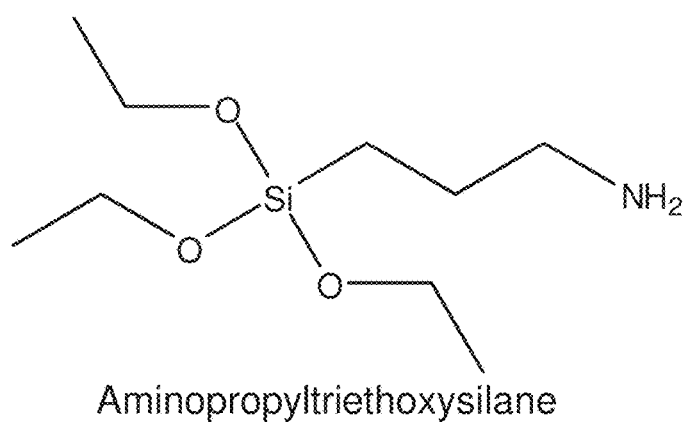
Figure 1A:
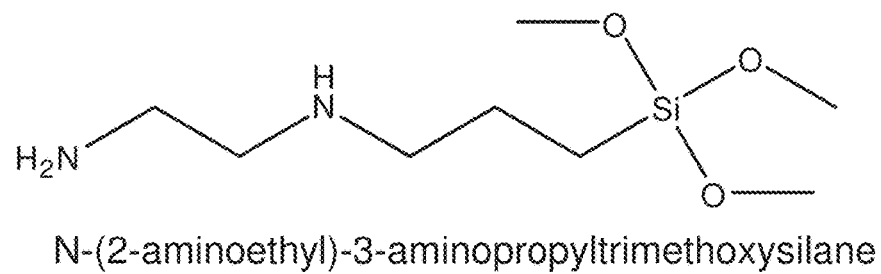
Figure 1A:
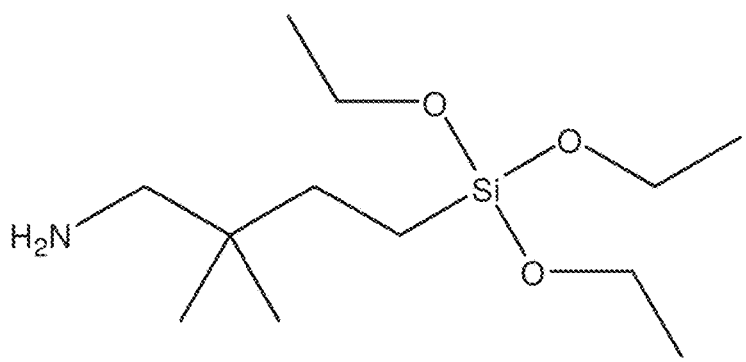
Figure 1B:
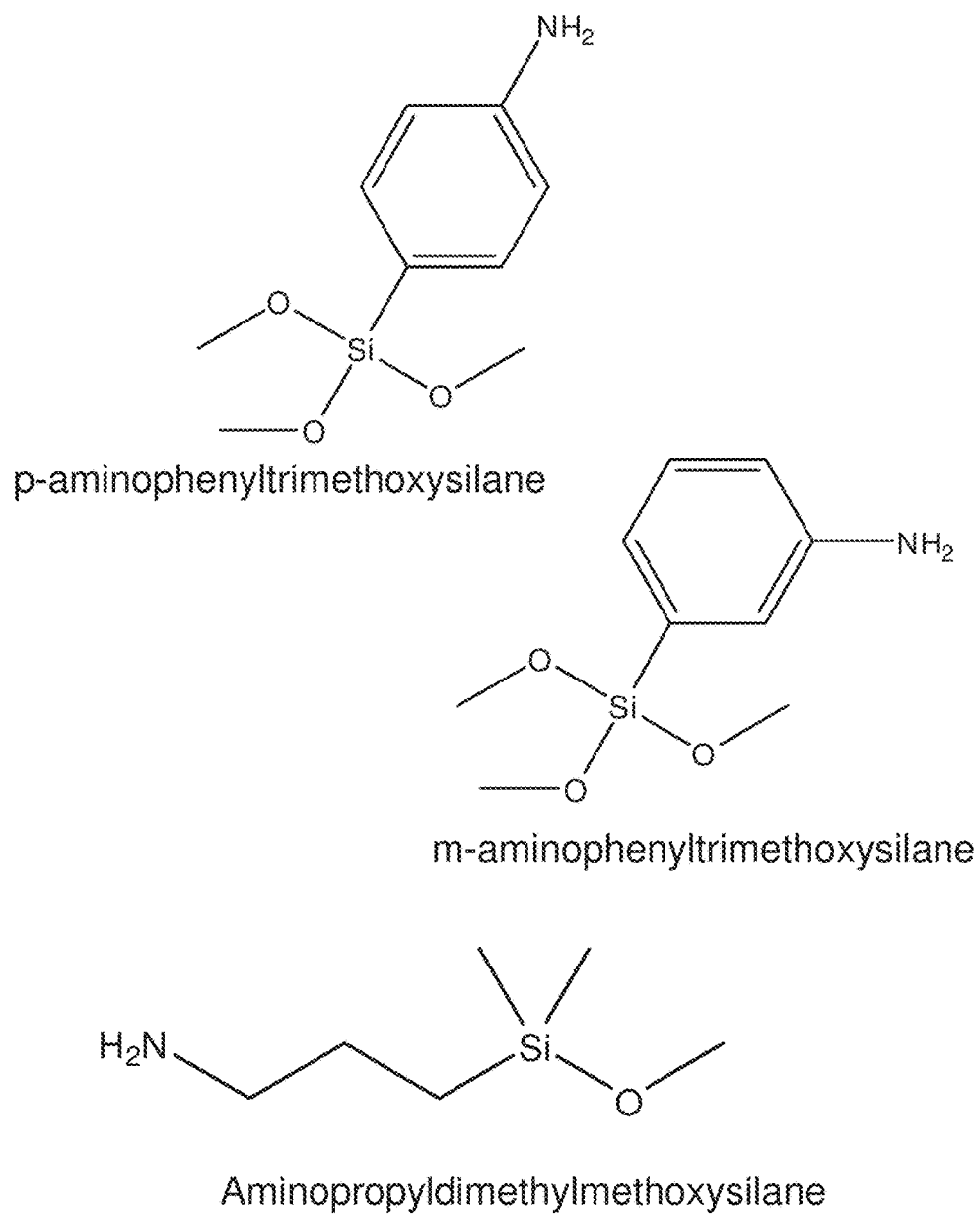
Figure 1C:
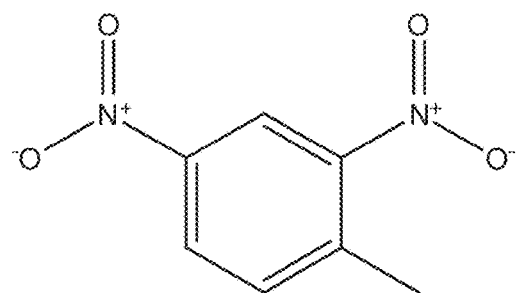
Figure 1C:
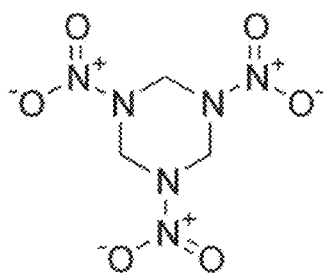
Figure 1C:
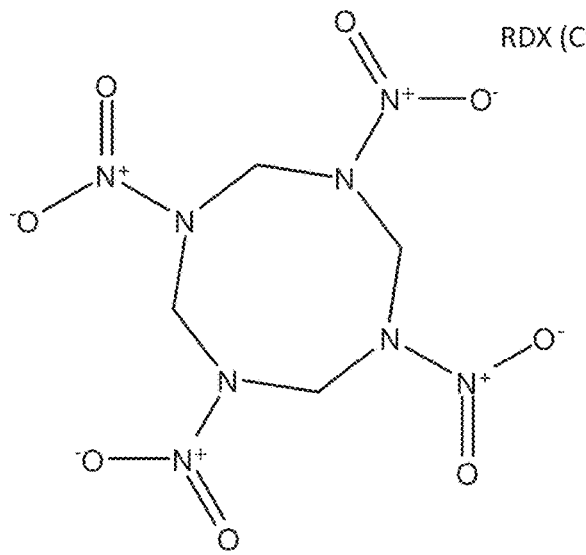
Figure 1D:
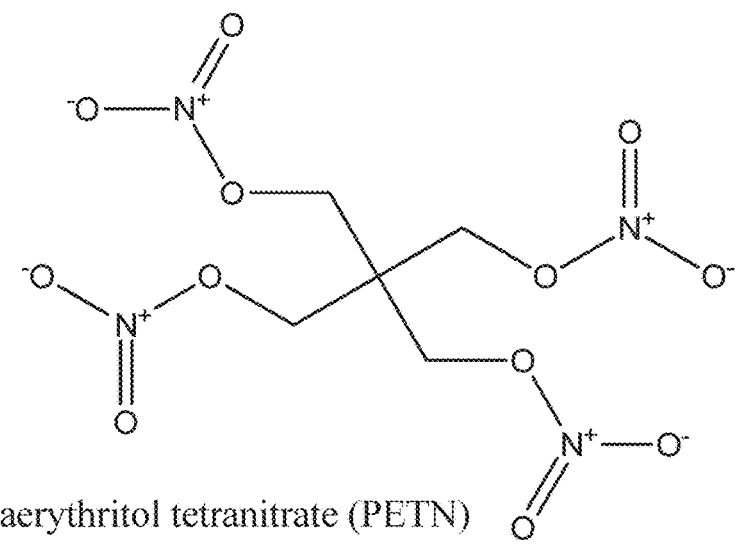
Figure 1D:
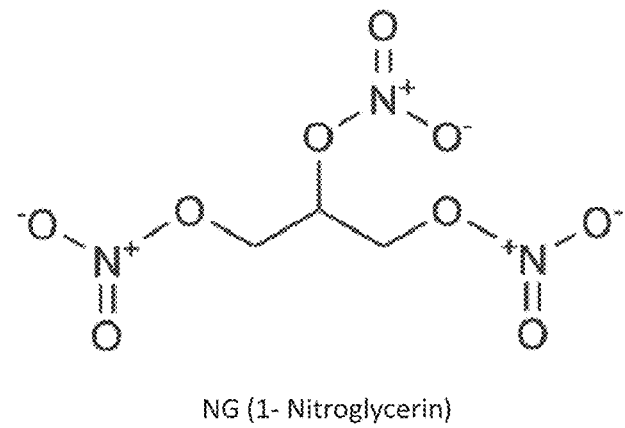
Figure 1E:
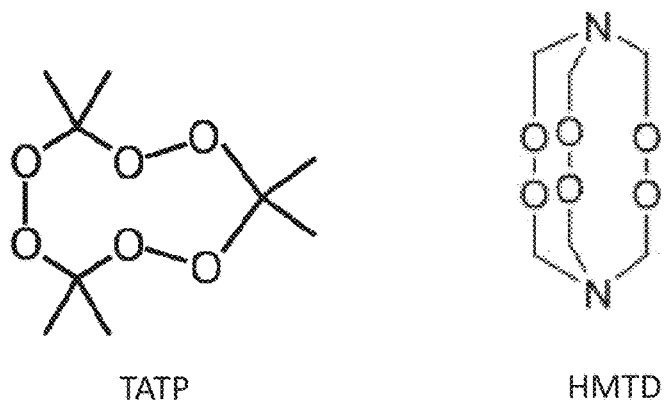
Figure 1E:
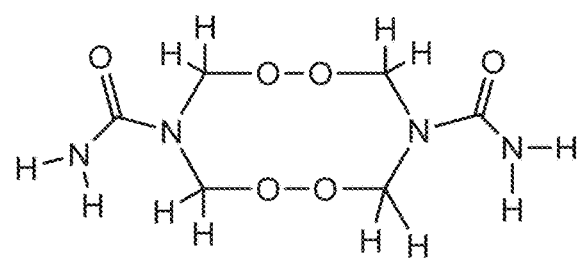

FIGS. 1A-E present chemical structures of exemplary silane derivatives used for modifying SiNWs according to some embodiments of the present invention (FIGS. 1A and 1B), of exemplary nitro-containing explosives (FIGS. 1C and 1D), and of exemplary peroxide-based explosives (FIG. 1E).

Figure 2:
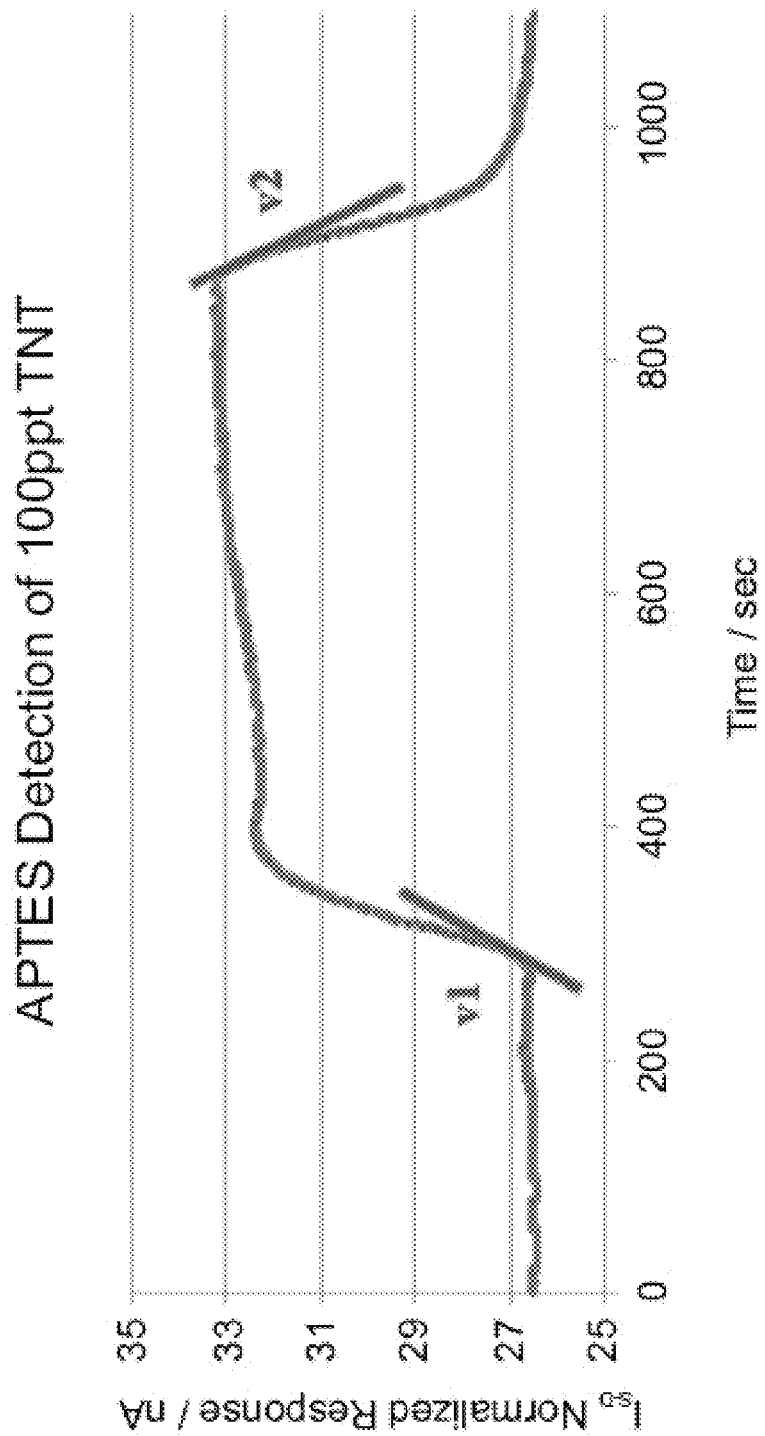

FIG. 2 presents an exemplary graph of the recorded $I_{SD}$/nA as a function of time, obtained for APTES-modified SiNW for detection of TNT, illustrating the initial kinetic slopes calculations: v1 (binding zone) and v2 (un-binding zone). In this graph, the value of v1/v2 is 0.9831.

Figure 3A:
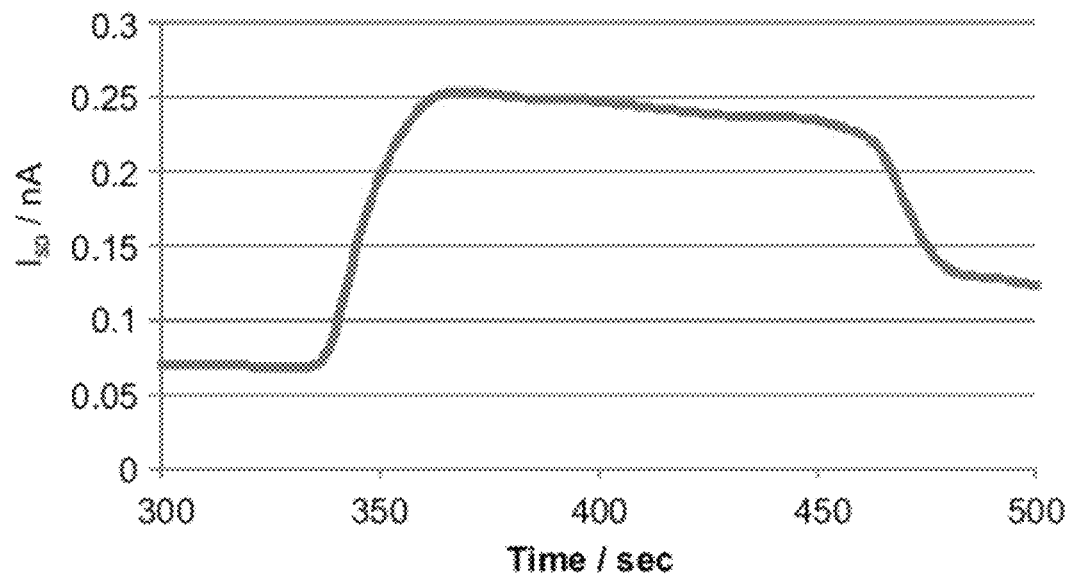
Figure 3B:
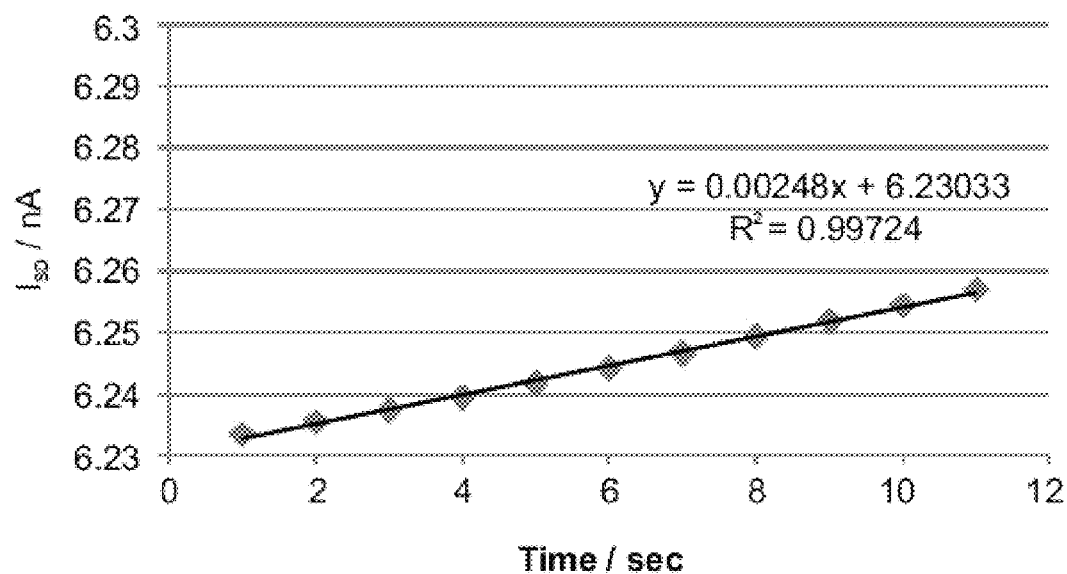
Figure 3C:
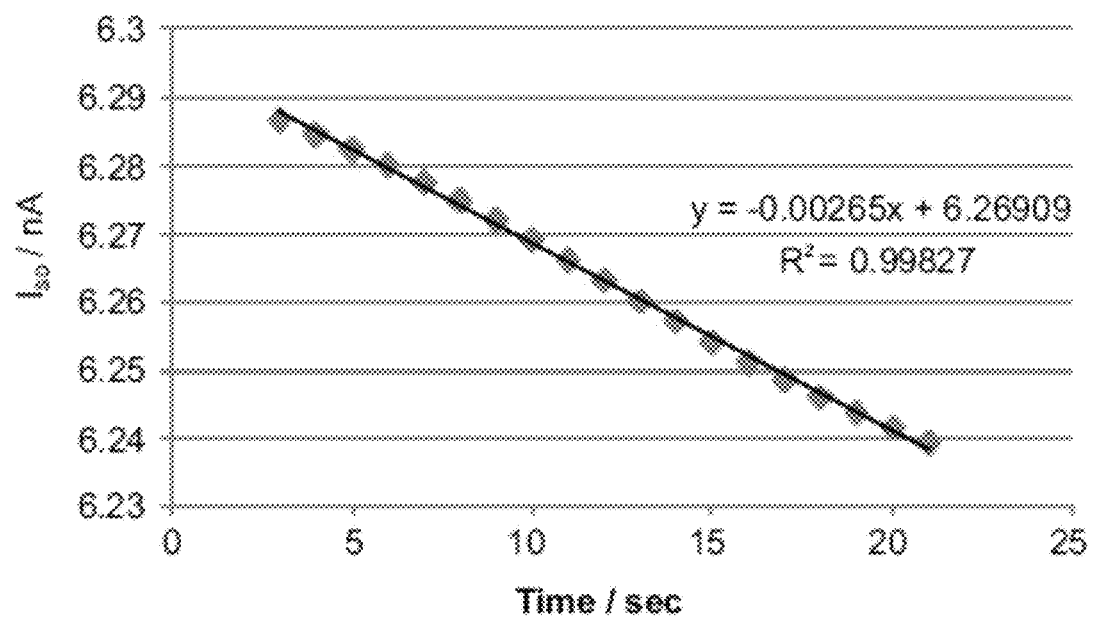

FIGS. 3A-C present exemplary graphs of the recorded $I_{SD}$/nA as a function of time, obtained for APTES-modified SiNW for detection of TNT, illustrating the general curve (FIG. 3A), binding (FIG. 3B) and unbinding (FIG. 3C) reactions. Slopes values are indicated near the graphs. The kinetic ratio (v1/v2) in this example equals 0.9358.

Figure 4:
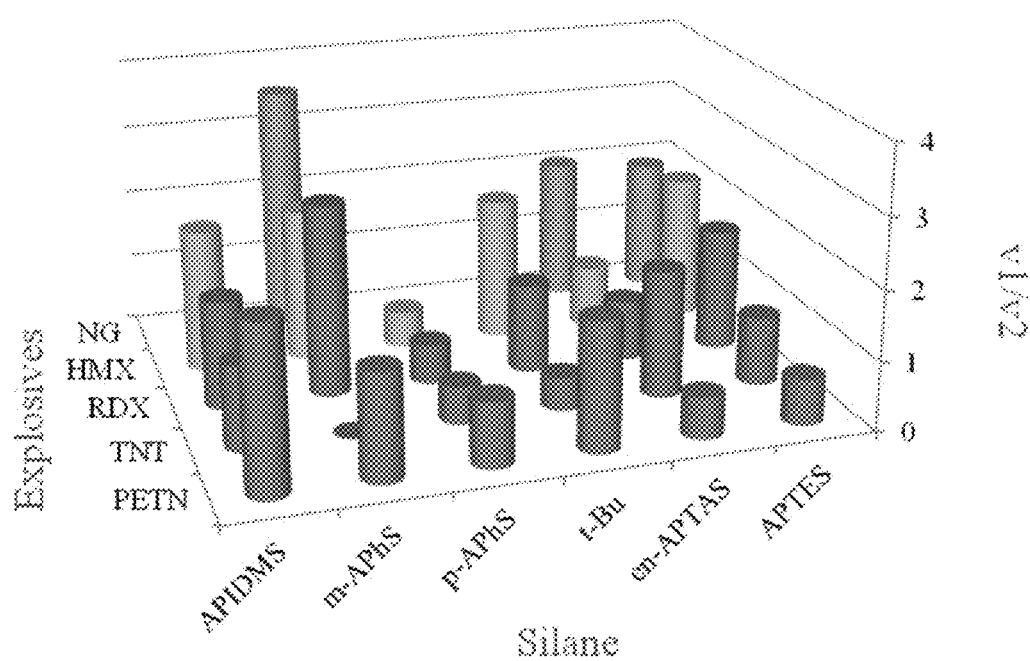

FIG. 4 presents initial kinetic slopes ratios: v1/v2 as a function of the tested explosive and the sensing modified-silane NWs.

Figure 5A:
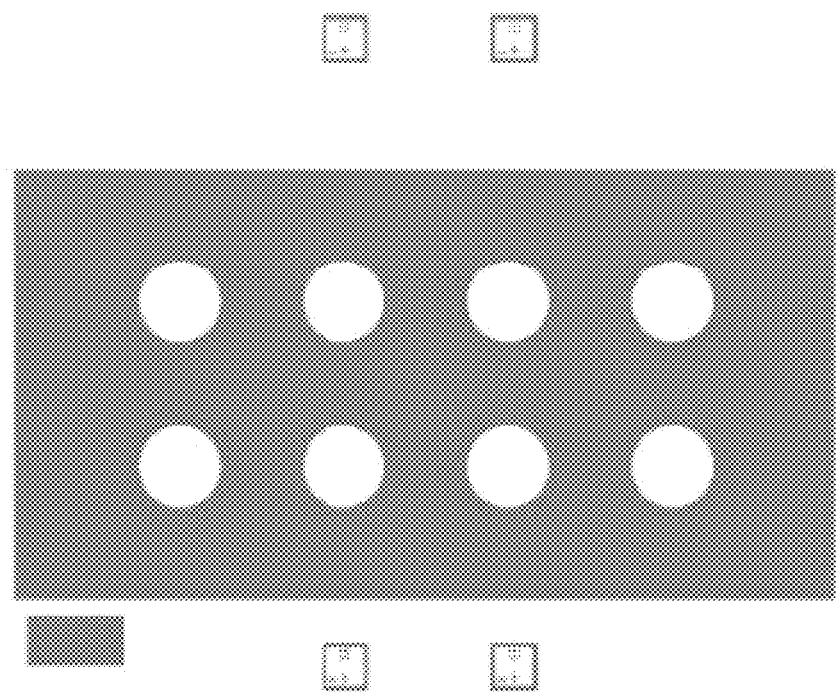
Figure 5B:
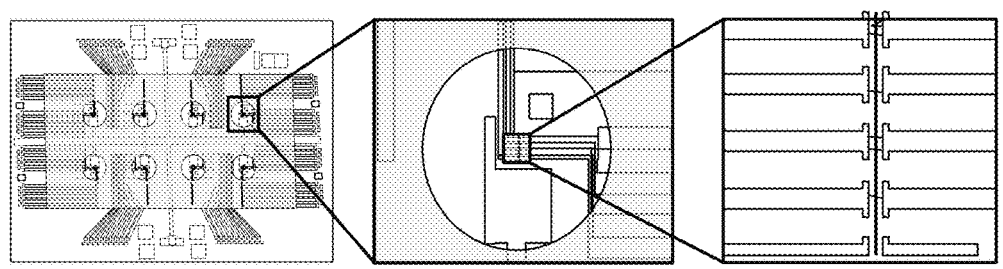
Figure 5C:
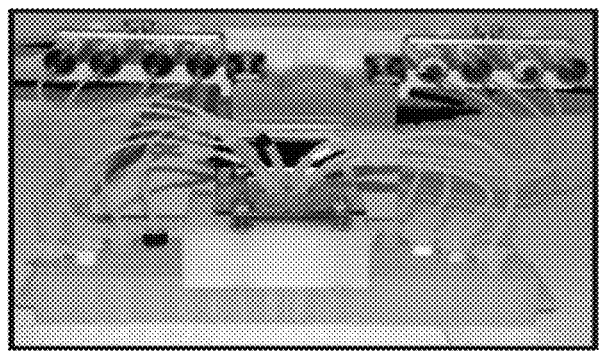
Figure 5D:
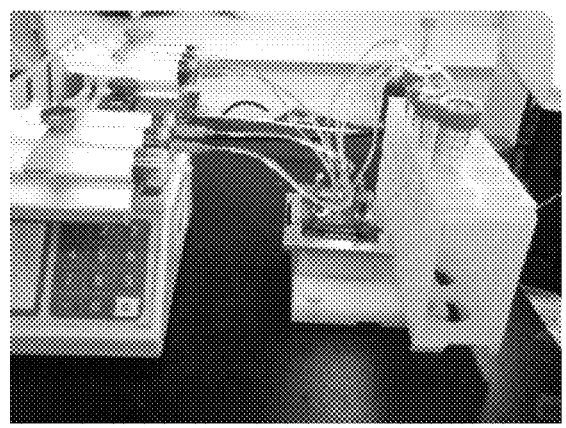

FIGS. 5A-D present Nn image of a SU-8 mask which can be used for defining eight active areas in a multi-array device according to some embodiments of the present invention (FIG. 5A); progressive enlargements of an exemplary single sensor, which can comprise one or more nanostructures, wherein p-doped SiNWs channels, bridge a common source (middle electrode) with its surrounding drain electrodes (FIG. 5B); and exemplary systems for forming variously modified arrays by simultaneously flowing different silane derivatives onto their designated arrays using a dedicated eight-channel fluidic device (FIGS. 5C and 5D).

Figure 6:
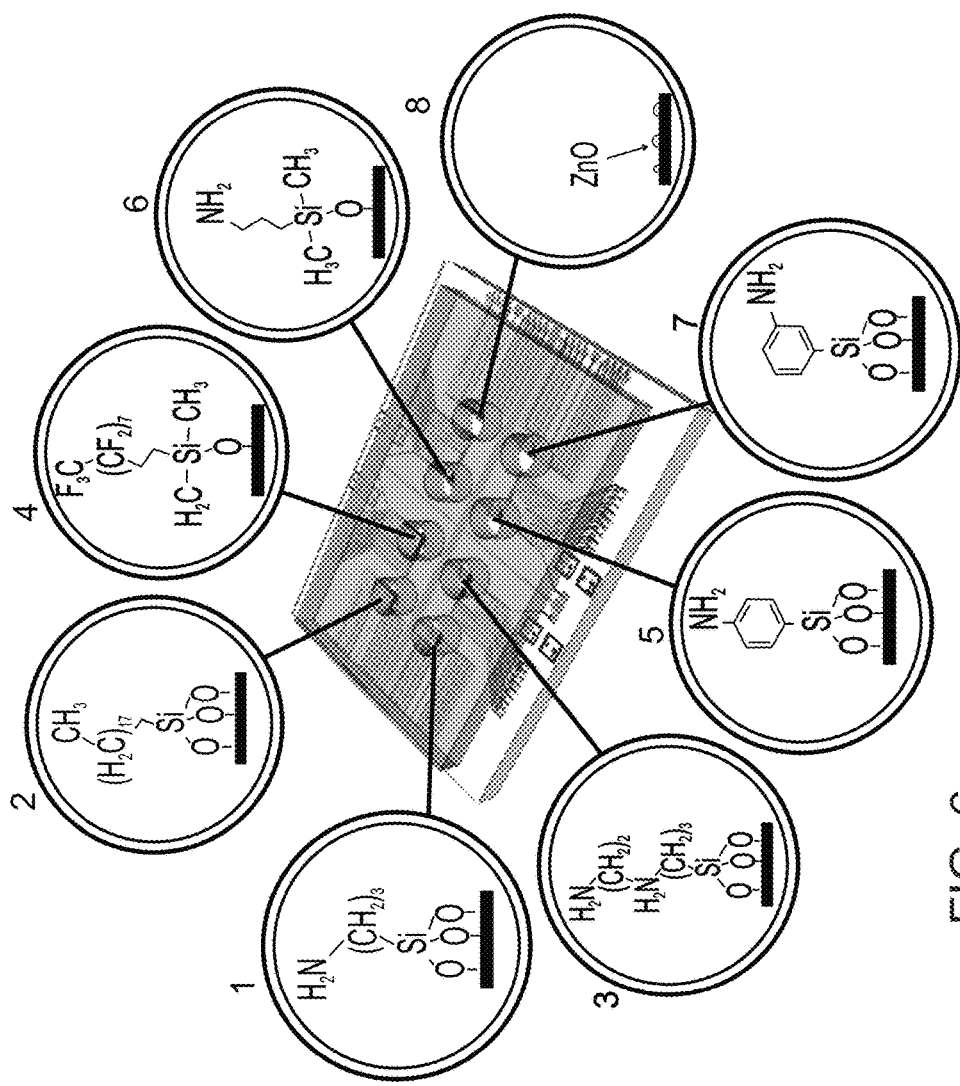

FIG. 6 presents a schematic illustration of a multi-array chip according to exemplary embodiments of the present invention, comprising eight differently-modified arrays as follows: (1) Aminopropyltriethoxysilane (APTES), (2) N-Octadecyltriethoxysilane (OTS), (3) n-(2-aminoethyl)-3-3aminopropyltrimethoxysilane, (en-APTAS), (4) (Heptadecafluoro- 1,1,2,2-tetrahydrodecyl)dimerhylchlorosilane (Flurosilane), (5) p-aminophenyltrimethoxysilane (p-APhS), (6) Aminopropyldimethylmethoxysilane (APDMES), (7) m-aminophenyl trimethoxysilane (m-APhS), (8) silicon oxide, non-modified SiNW.

Figure 7A:
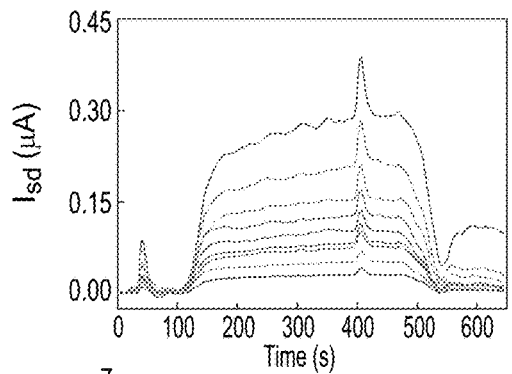
Figure 7B:
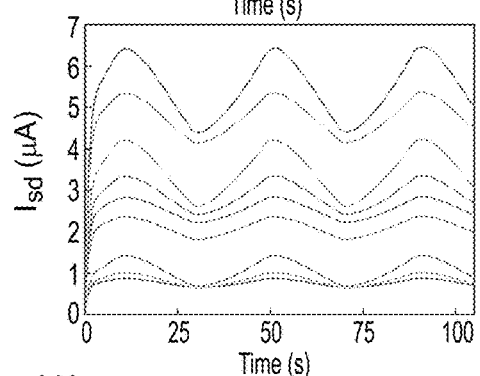
Figure 7C:
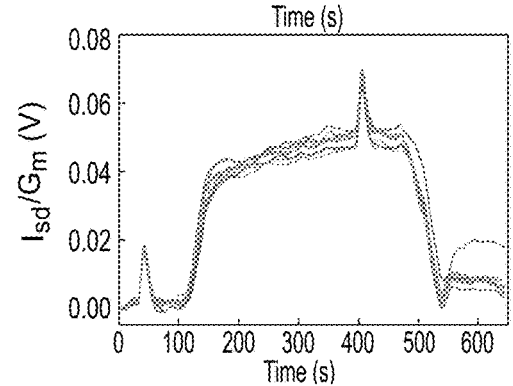
Figure 7D:
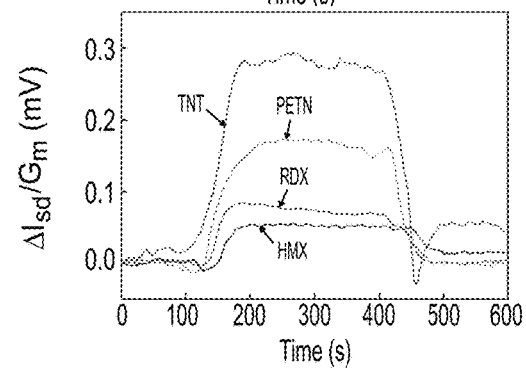

FIGS. 7A-D present exemplary signal processing operations, according to some embodiments of the present invention, demonstrated on sensing of TNT by 9 APTES-modified active sensing devices. FIG. 7A presents the raw sensing response to TNT over time of the APTES-modified active sensing devices. FIG. 7B presents the transconductance response of the same sensing devices as a function of the gate voltage being periodically modulated between −0.3V and +0.3V. FIG. 7C presents calibration of the responses presented in FIG. 7A, after dividing each device raw response by its gate dependence ($dI_{DS}/dV_G$). After calibration, all 9 devices display similar electrical behavior. FIG. 7D presents calibrated responses of a representative APTES-modified sensing device to different explosive species at the same concentration.

Figure 8A:
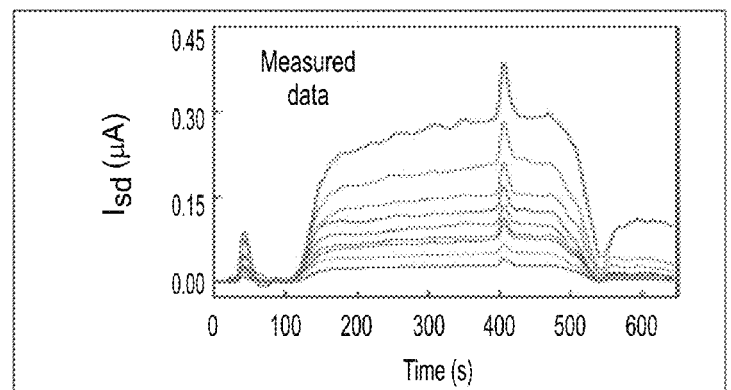
Figure 8B:
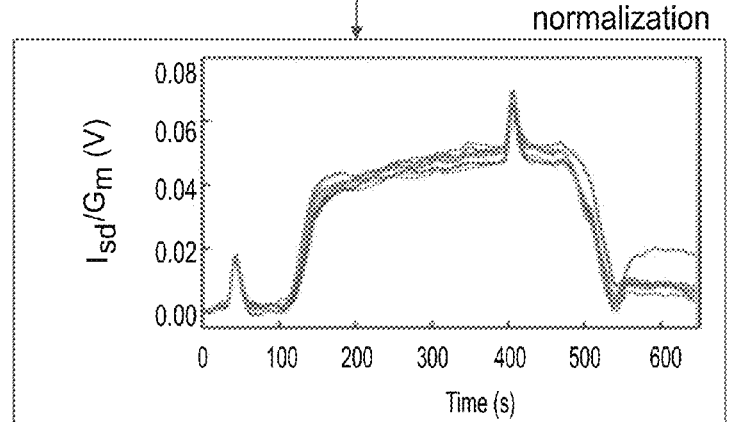
Figure 8C:
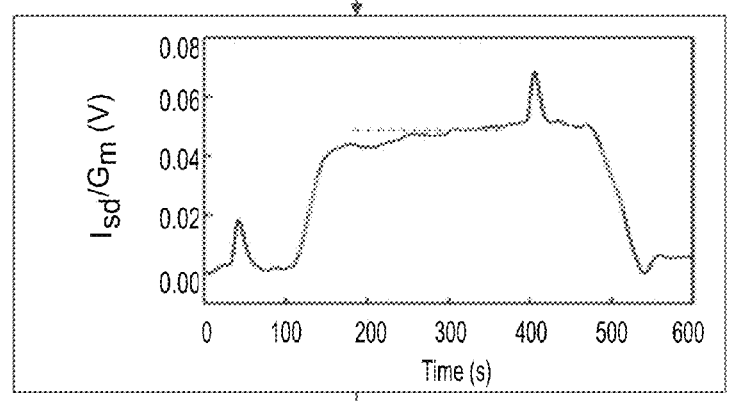
Figure 8D:
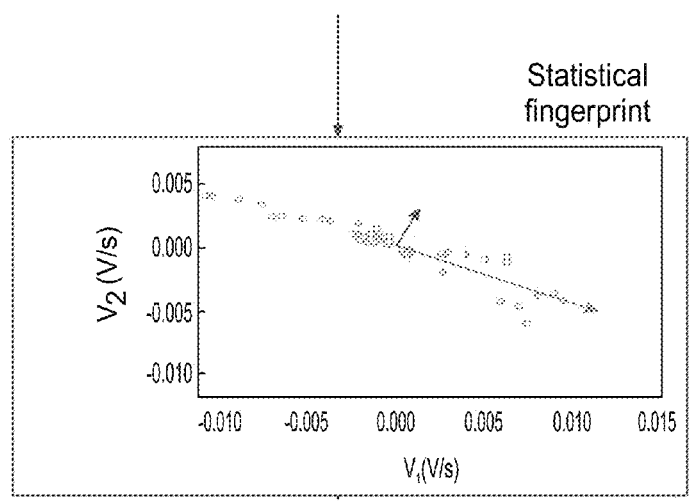
Figure 8E:
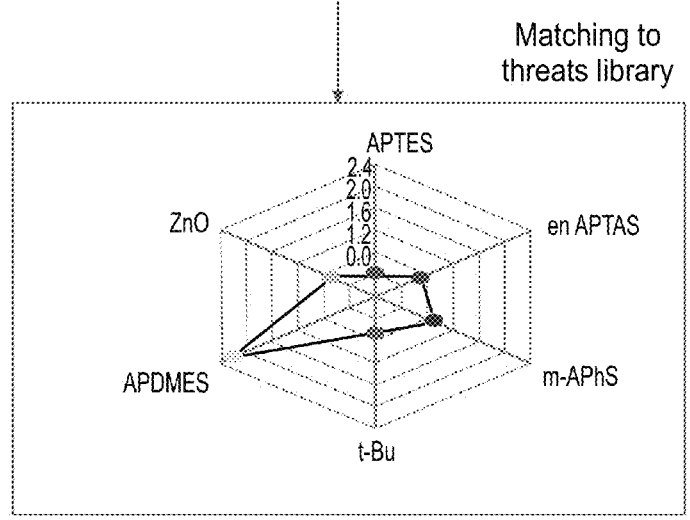
Figure 9A:
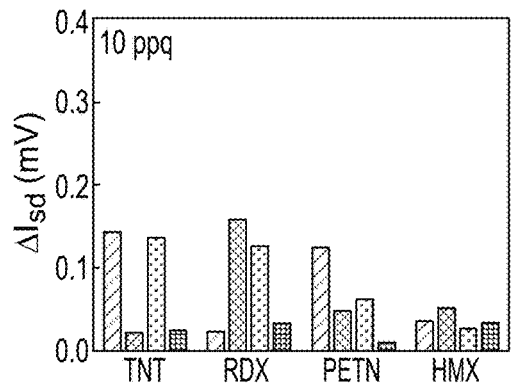
Figure 9B:
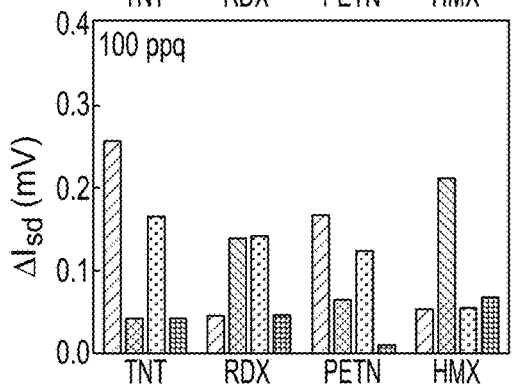
Figure 9C:
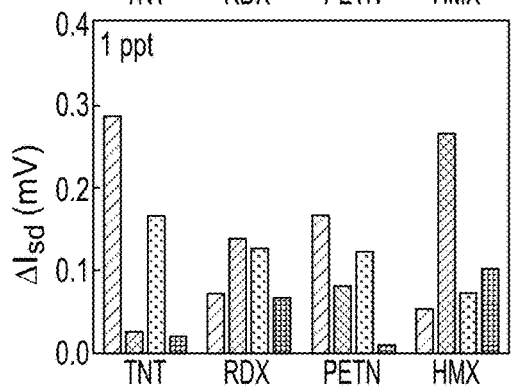
Figure 9D:
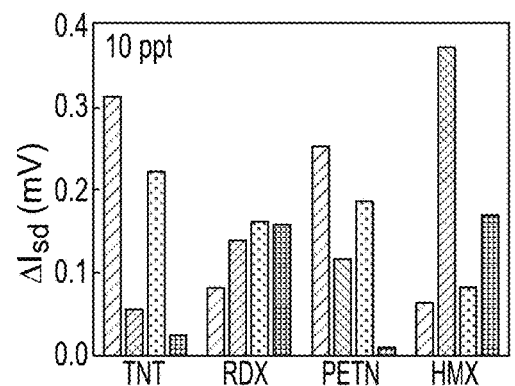
Figure 10A:
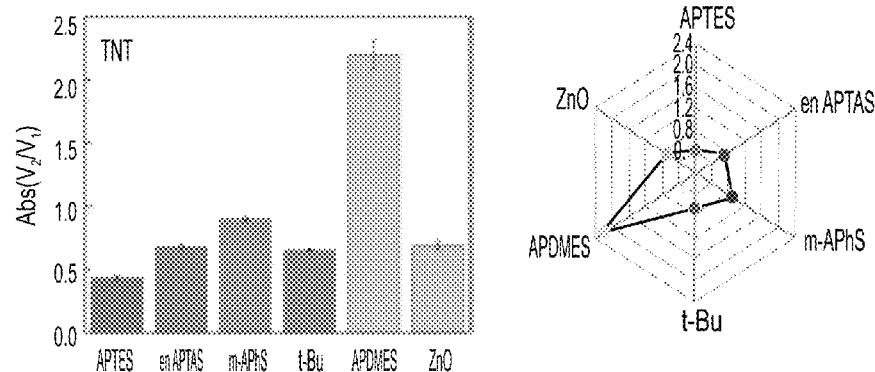
Figure 10B:
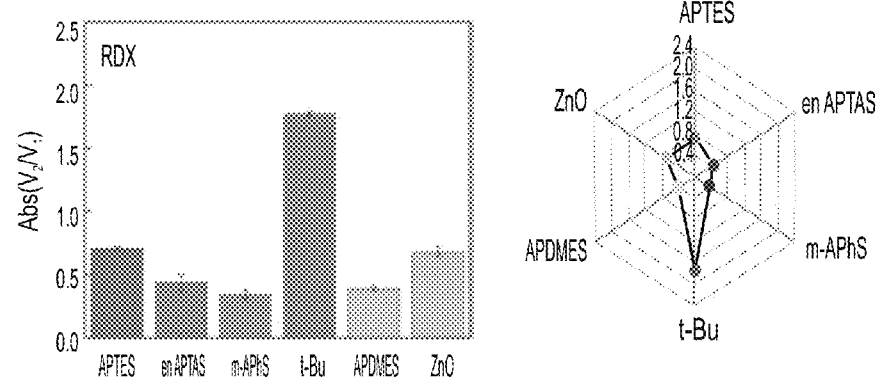
Figure 10C:
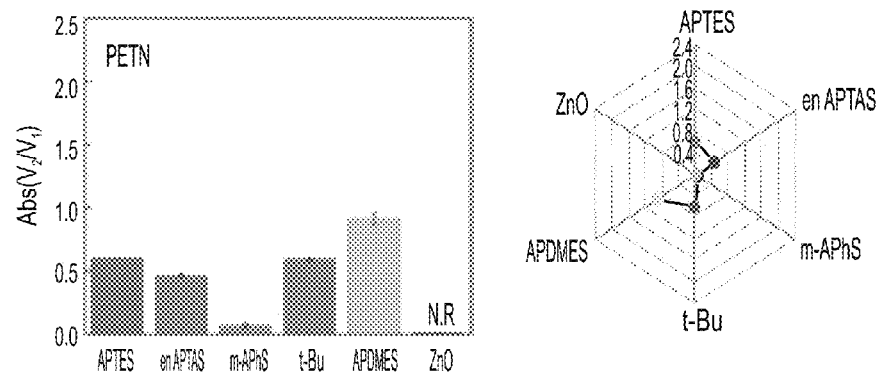
Figure 10D:
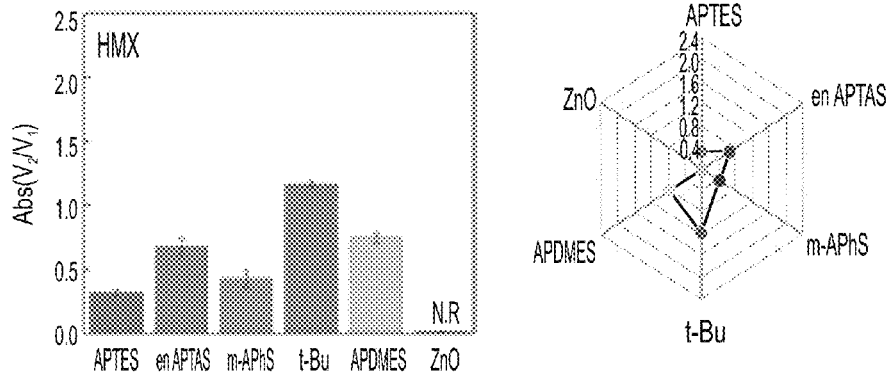
Figure 10E:
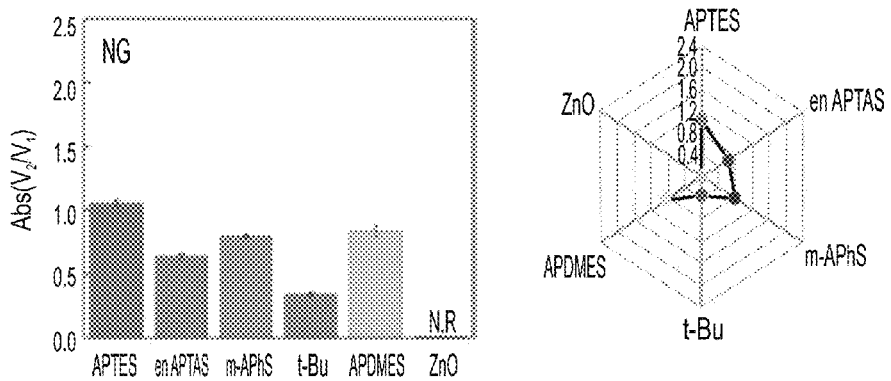
Figure 10F:
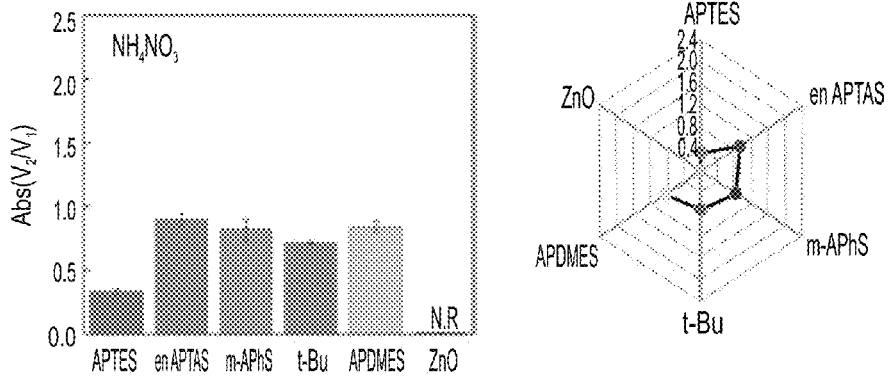

FIGS. 8A-E present exemplary signal processing operations, according to some embodiments of the present invention, demonstrated on sensing of TNT by 9 APTES-modified active sensing devices. FIG. 8A presents the raw response data. FIG. 8B presents calibrating each device's absolute raw response against its gate dependence ($dI_{DS}/dV_G$). FIG. 8C presents mathematical extraction of the following parameters: the kinetic ratio (v1/v2) and the calibrated absolute response under steady state conditions. FIG. 8D presents further data processing, whereby the statistical dependence of the kinetic constants is globally estimated by the slope of a straight line in the v1-v2 plane obtained by regression using R-square as a target function, taking into account all accumulated v1-v2 pairs. FIG. 8E presents chemical identification wherein a matching is done between the pattern generated by the given ensemble response to a library of previously calculated responses.

FIGS. 9A-D present the calibrated absolute responses, at a steady state, of SiNWs differently modified by different silane derivatives (APTES: Aminopropyltriethoxysilane (blue), en-APTAS: n-(2-aminoethyl)-3-3aminopropyltrimethoxysilane (red), p-APhS: p-aminophenyltrimethoxysilane (green), t-Bu: 4-amino-3,3-dimethylbuthyltriethoxysilane (purple), to different nitro-containing explosive (TNT, RDX, HMX, PETN), at a concentration of 10 ppq (FIG. 9A), 100 ppq (FIG. 9B), 1 ppt (FIG. 9C) and 10 ppt (FIG. 9D), demonstrating that the relative responses create a concentration independent pattern to make an explosive's unique fingerprint.

FIGS. 10A-F present exemplary algorithm-derived kinetic ratios of real-time measured transient electrical signals (v1/v2) map, generated for TNT (FIG. 10A), RDX (FIG. 10B), PETN (FIG. 10C), HMX (FIG. 10D), NG (FIG. 10E) and nitrate ions ($NH_4NO_3$) (FIG. 10F), using multiarray chips, each bearing differently modified SiNWs in which SiNWs were modified by APTES: Aminopropyltriethoxysilane (blue), en-APTAS: n-(2-aminoethyl)-3-3aminopropyltrimethoxysilane (red), p-APhS: p-aminophenyltrimethoxysilane (green), t-Bu: 4-amino-3,3-dimethylbuthyltriethoxysilane (purple), APDMES: Aminopropyldimethylmethoxysilane (yellow) and ZnO (zinc oxide-decorated SiNWs) (gray)). The whole set of mathematically-derived kinetics produces a profile library (left panel, bar graph), where each result is calculated over more than 50 experiments performed with at least 5 different chips. A unique fingerprint pattern that enables the discrimination of all tested explosives is generated as shown by the 'radar plot' two-dimensional presentations on the right panel).

Figure 11:
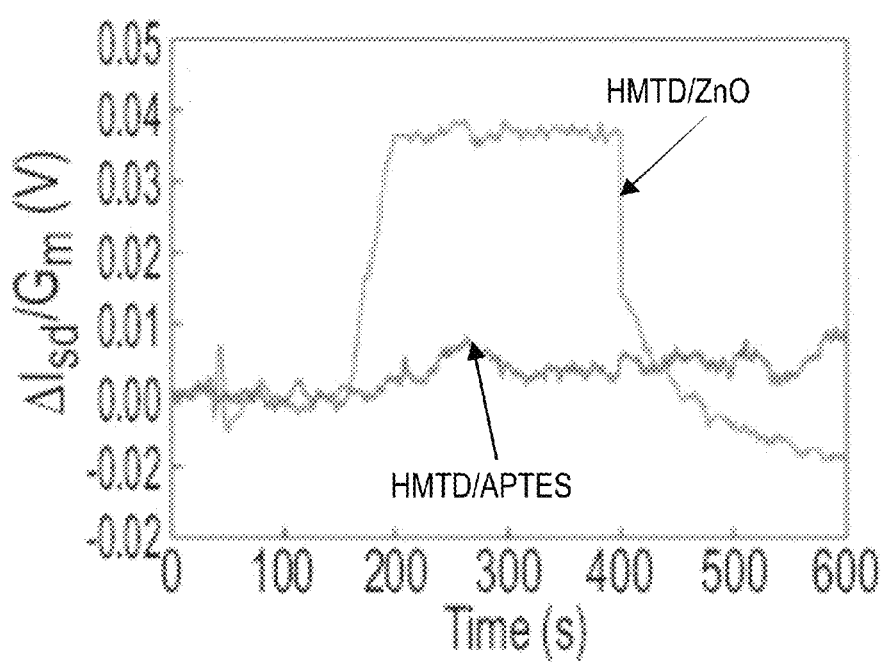

FIG. 11 presents the raw response data of APTES-modified SiNWs (blue) and of ZnO-nodified SiNW (red) to HMDT at a concentration of 1 ppt, demonstrating the insensitivity of silane derivative-modified SiNWs to the peroxide-based explosives family.

Figure 12:
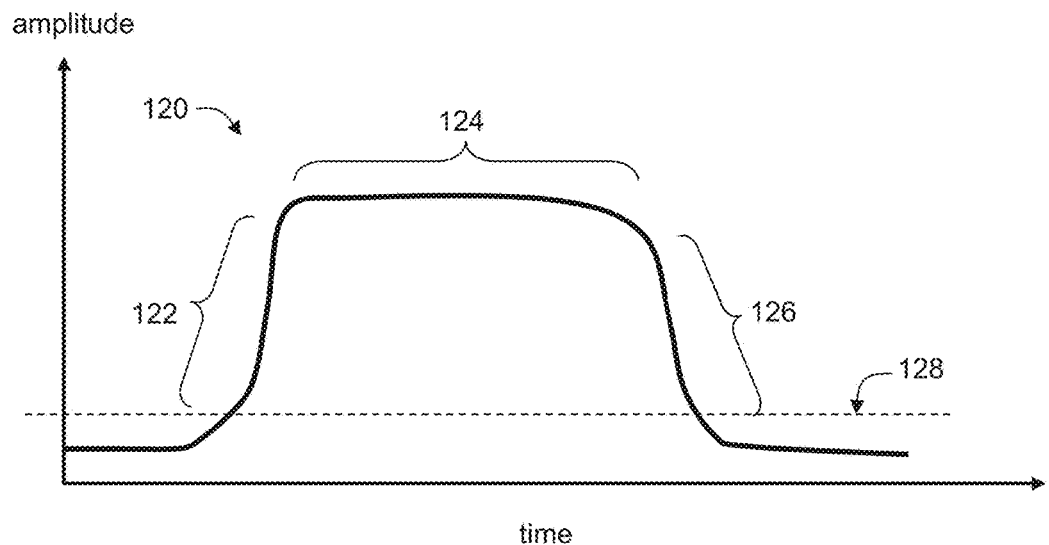

FIG. 12 is a schematic illustration of a signal that is generated by a sensing device of an explosive identification system according to some embodiments of the present invention.

Figure 13:
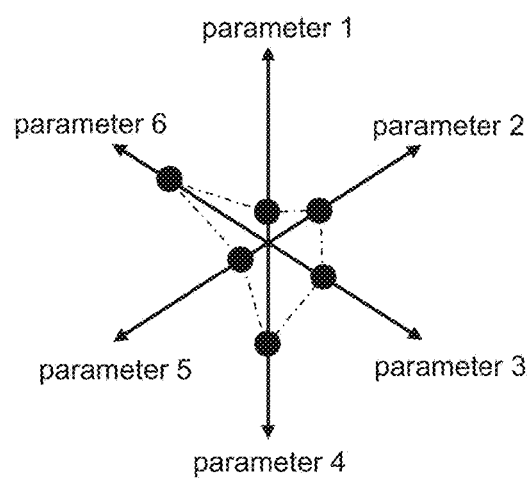

FIG. 13 is a schematic illustration of a graphical presentation of an explosive fingerprint, according to some embodiments of the present invention.

Figure 14:
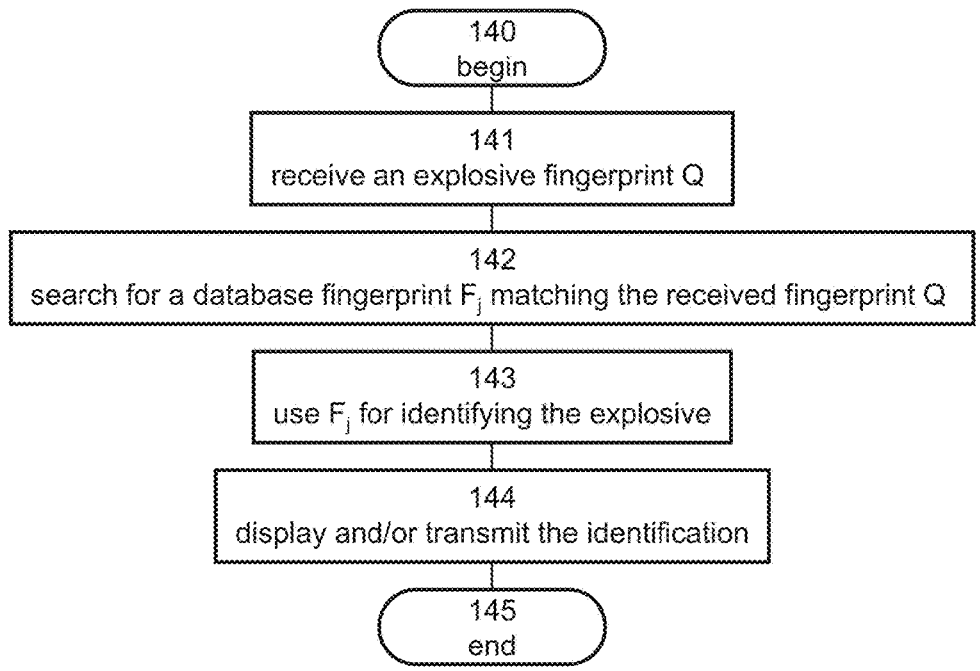

FIG. 14 is a flowchart diagram describing a method suitable for identifying an explosive in a sample, according to some embodiments of the present invention.

Figure 15:
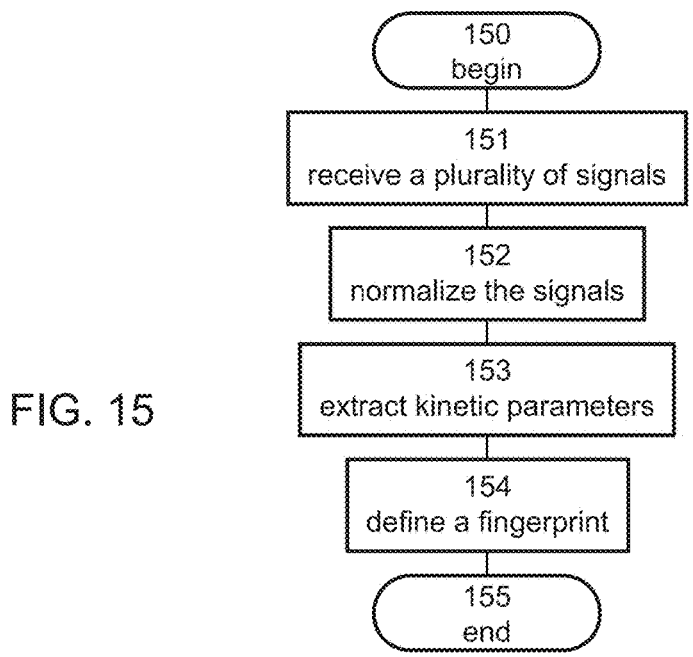

FIG. 15 is a flowchart diagram illustrating a procedure suitable for constructing a fingerprint of an explosive in an explosive containing sample, according to some embodiments of the present invention.

Figure 16:
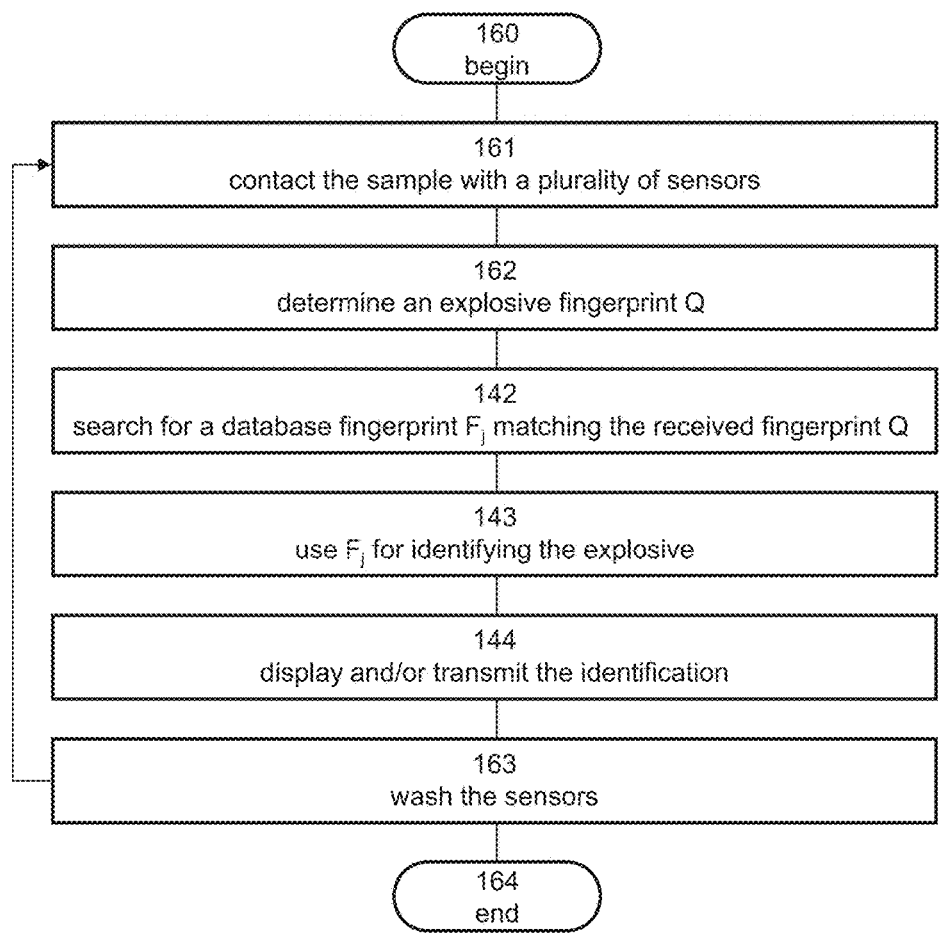

FIG. 16 is a flowchart diagram illustrating a method suitable for identifying an unidentified explosive in an explosive containing sample, according to some embodiments of the present invention.

Figure 17:
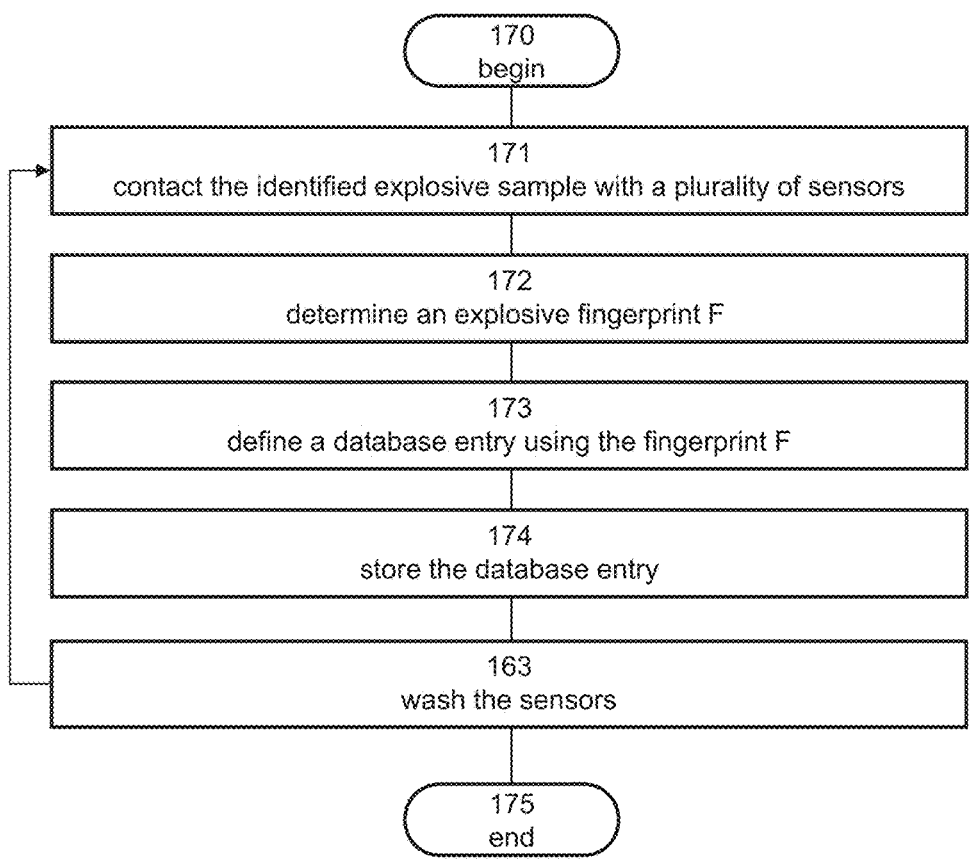

FIG. 17 is a flowchart diagram illustrating a method suitable for constructing a database of explosive fingerprints, according to some embodiments of the present invention.

Figure 18:
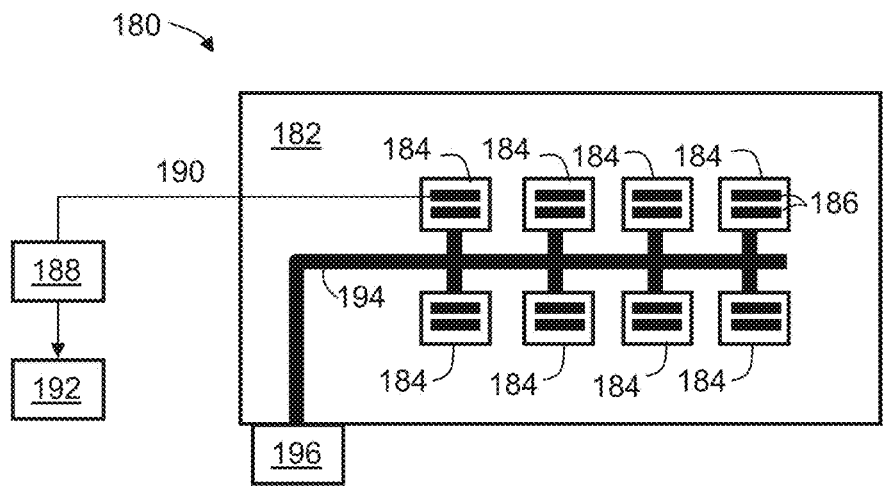

FIG. 18 is a schematic illustration of a system, according to some embodiments of the present invention. The system can be used for determining the presence of an explosive, and optionally also for identifying the explosive.

Figure 19:
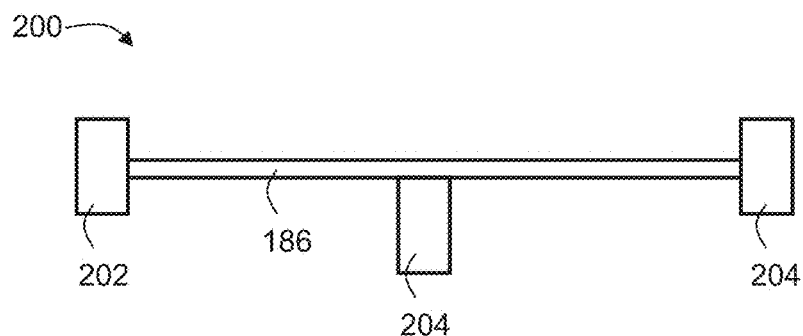

FIG. 19 is a schematic illustration of a nanostructure in embodiment of the present invention in which the nanostructure forms a transistor.

Figure 20A:
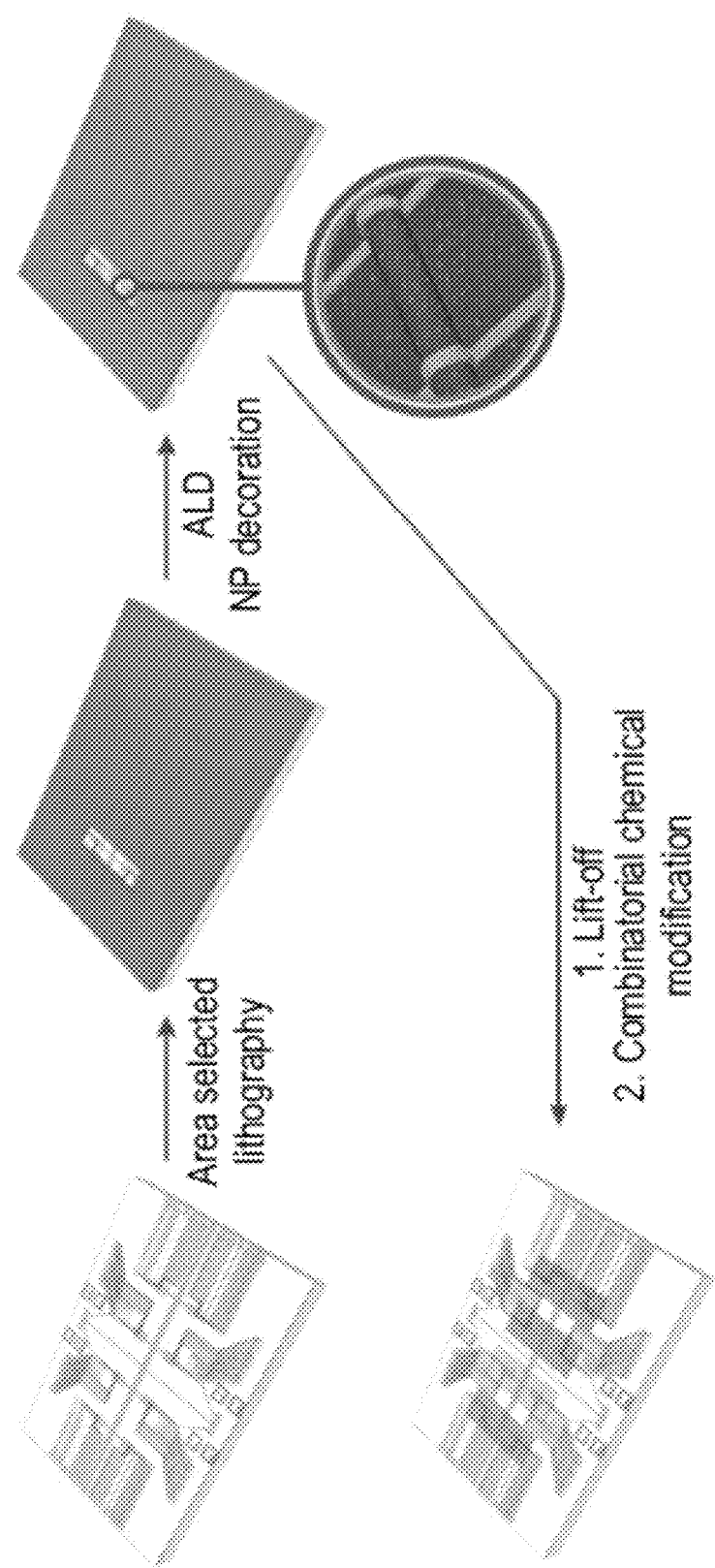
Figure 20B:
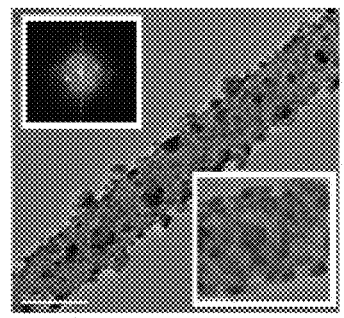

FIGS. 20A-B present an exemplary area-dedicated sensing regions on a multiarray chip generated by the ALD-assisted decoration of ZnO nanoparticles of Si nanoFETs, followed by resist removal to lay bare other sub-regions, to be in turn, chemically-modified selectively with e.g., silane derivatives, as described, for example, in FIG. 6 (FIG. 20A); and a representative TEM image of ALD-deposited zinc oxide nanoparticles (70° C., 10 cycles) decorating p-type SiNWs (about 20 nm diameter) (FIG. 20B).

Figure 21:
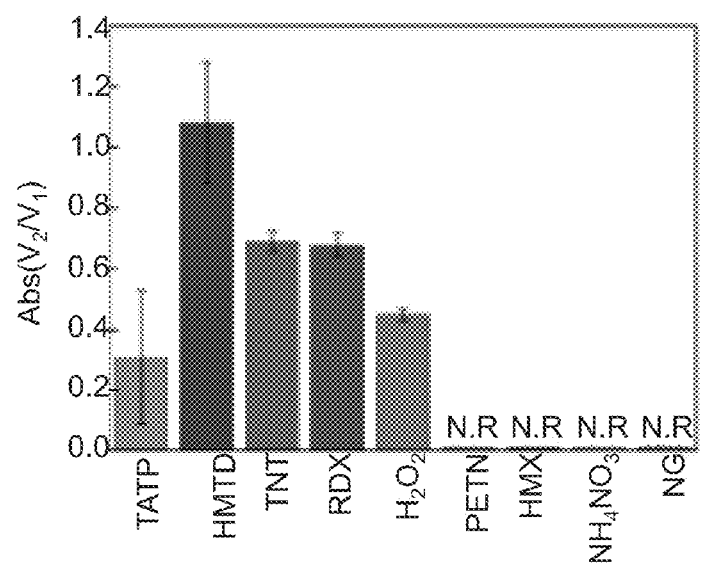

FIG. 21 presents a bar graph showing the kinetic ratio, calculated as described herein, of various explosives with ZnO-modified SiNWs, showing that ZnO complex with six-membered rings of TNT and RDX, yet is inert to the eight-membered ring of HMX and the linear structured nitro-containing explosives (PETN, NG). $H_2O_2$ is detected only at 250 ppm. Irrespective of their concentration all explosives are discriminated through their respective kinetic ratio.

DESCRIPTION OF SPECIFIC EMBODIMENTS OF THE INVENTION

The present invention, in some embodiments thereof, relates to detection of chemicals and, more particularly, but not exclusively, to devices, systems and methods useful for detecting and identifying explosives.

The present inventors have now devised and successfully prepared and practiced a system, which can be efficiently used for detecting the presence of, and optionally and preferably also identifying, an explosive.

By "identifying" it is meant that an identity of an explosive is determined, namely, a specific explosive, as defined herein, is identified and discriminated from another explosive or from non-explosive, chemically-related compounds or mixtures of compounds.

Presented herein is an ultra-sensitive and highly selective platform for the detection and discriminative identification of chemical species such as explosives, based on the use of large-scale arrays of combinatorially-modified electrical nanosensors, defining a plurality of multiple functional reaction sites enabling a high throughput assay. When modified in a combinatorial mode, by association with multiple non-specific functional groups, nanostructure-based arrays such as nanowire-based field-effect-transistor arrays (NW-FETs) enable a supersensitive discriminative detection, fingerprinting, of multiple explosive compounds, down to the parts-per-quadrillion concentration range.

The differential identification between explosives presented herein is achieved by pattern recognition of the naturally inherent interaction, both kinetically and thermodynamically, between the combinatorially-modified nanostructure multi-array and the explosives. A unique explosives fingerprinting database is therefore also presented herein, enabling to set apart similar chemical entities, and providing a fast and reliable method to identify individual explosives, while avoiding confusion with common potential interfering materials.

The multiplexed identification of explosives disclosed herein is exemplified by arrays of SiNW-FETs, each group of SiNW-FETs being surface-modified uniquely by a different surface functional group. The simultaneous interaction of a sample with all surface functional groups is profiled by a set of kinetics. When a specific gate voltage is imposed, the drain current varies and the channel conductance disappears according to explosive-surface functional group pair.

The system disclosed herein was demonstrated to perform super-sensitive and selective real-time detection of explosives, including nitro- and peroxide-containing explosives, on a single electronic platform, chemically modified in a combinatorial mode. The system of the present embodiments allows for the detection of all tested explosives, from air, liquid or solid (e.g., particles) samples, down to the parts-per-quadrillion concentration range in a few seconds of analysis. The system of the present embodiments comprises a plurality of sensing devices employing nanotechnology. The system identifies explosives, by multidimensional comparison between a detected fingerprint and a database fingerprint. In various exemplary embodiments of the invention the sensitivity featured by the individual sensing devices of the system is maintained. In other words, the sensitivity of the system equals to or better than the sensitivity of the individual sensing devices.

The term "sensitivity" is used herein to characterize an explosive identification system and relates to the lowest concentration of an explosive in an explosive containing sample that is identifiable by the system.

As used herein the expression "sensitivity threshold" means the concentration of an explosive in a sample below which the explosive cannot be detected in the sample by the system. Thus, the sensitivity threshold characterizes the sensitivity of the explosive identification system. In relative terms, higher values of the sensitivity threshold correspond to lower sensitivity of the system, and lower values of the sensitivity threshold correspond to higher sensitivity of the system.

In some embodiments of the present invention the sensitivity threshold of the explosive identification system, when expressed as mole fraction, is less than 1 parts-per-million (ppm) or less than 1 parts-per-billion (ppb) or less than 1 parts-per-trillion ppt, e.g., 1 parts-per-quadrillion (ppq).

The present inventors have also devised and successfully prepared and practiced a sensitive rapid detection of peroxide-based improvised explosive species, such as, for example, TATP and HMTD, which can be performed by the deposition of metal oxide nanoparticles (NP) on nanostructures.

By means of, for example, an area-selected lithography procedure, the fabrication and efficient performance of combinatorial sensing multi-arrays comprising differently modified nanostructures altogether in a single detection platform, was demonstrated.

The systems and methods disclosed herein are usable for constructing and operating a searchable database which can be used for determining the presence and optionally also identifying an explosive in a sample.

The Database:

The present embodiments comprise a searchable database which can be used for determining the presence and optionally also identifying the explosive. The present embodiments further comprise a computer readable non-volatile data storage medium carrying the database.

The database of some embodiments of the present invention comprises a plurality of entries, where each entry j has an explosive fingerprint $F_j$ and an explosive classifier $C_j$ associated to the fingerprint $F_j$. The explosive fingerprint $F_j$ is preferably in the form of a set of parameters, optionally and preferably a set of kinetic parameters as further detailed hereinbelow. The classifier $C_j$ can be, for example, the name of the explosive (e.g., TNT, RDX, HMX, PETN, NG), or the name of a class of explosives (e.g., nitroaromatic-based explosives, nitramine-based explosives, nitrate ester-based explosives, inorganic nitrate-based explosives, chlorate-based explosives, perchlorate-based explosives, bromate-based explosives, peroxide-based explosives, smokeless powder-based explosives and black-powder-based explosives).

The database of the present embodiments can be embodied in any computer readable non-volatile data storage medium, including, without limitation, a memory medium (e.g., RAM, ROM, EEPROM, flash memory, etc.), an optical storage medium (e.g., CD-ROM, DVD, etc.), a magnetic storage medium (e.g., magnetic cassettes, magnetic tape, magnetic disk storage device, etc.), or any other non-volatile medium which can be used to store the fingerprints and associated classifiers, and which can be accessed electronically, e.g., by a data processor. Some embodiments of the present invention contemplate an explosive database which is embodied on a printed medium.

The number of entries in the database of the present embodiments is referred to herein as the size V of the database. There is no limitation on the numerical value of V. Preferably, the number of entries is large so as to facilitate classification of many types of explosives. According to a preferred embodiment of the present invention the database comprises at least T entries (i.e., $V \geq T$), where T can be any number disclosed either explicitly or implicitly in the specification.

If desired, the database can be parsimonious in the sense that its size V is reduced compared to the size $V_t$ of a training group used for constructing the database. This embodiment is advantageous from the standpoint of data storage volume and/or processing time. The size of the database can be reduced, for example, by introducing further screening to the database according to additional information. For example, a parsimonious database can be obtained from a larger database by screening the larger database according to laboratory tests performed on known explosives, such as the explosives from which the entries of the larger database were extracted.

The advantage of the database of the present embodiments is in its canonical sets of parameters that are used to define the database explosive fingerprints. The present inventors have found that it is sufficient to attribute classification information to a target explosive based on a relatively small number of parameters. In various exemplary embodiments of the invention at least one, more preferably each, of the database fingerprint comprises less than L parameters, where L is an integer which is typically not larger than 15, e.g., L=2, L=3, L=4, L=5, L=6, L=7, L=8, L=9, L=10, L=11, L=12, L=13, L=14 or L=15. The number of parameters in the set is referred to herein as the size of the fingerprint.

For any fingerprint entry of the database, the set of parameters that define the fingerprint preferably describes a plurality of interactions between the explosive and each of a respective plurality of functional moieties. Each interaction can be described by one or more parameters. In some embodiments of the present invention each interaction is described by only one parameter, in some embodiments of the present invention each interaction is described by two parameters, and in some embodiments of the present invention each interaction is described by three parameters. Use of more than three parameters to describe the interaction is also contemplated.

In various exemplary embodiments of the invention the parameters comprise kinetic parameters.

As used herein "kinetic parameter" refers to a parameter that describes the interaction from the standpoint of the governing kinetics, as manifested by the sensing device that is used for sensing the explosive.

Typically, but not necessarily, a kinetic parameter relates to the time-dependence of the interaction between the explosive and the functional moiety. For example, the interaction between the explosive and the functional moiety can be defined as a three-stage sequential process, wherein a first stage is a transition from a state in which the sensing device does not generate a signal to a state in which the sensing device generates a generally steady state signal, a second stage is characterized by a generally steady state signal generated by the sensing device, and a third state is a transition from a state in which the sensing device generates a generally steady state signal to a state in which the sensing device does not generate a signal. In these embodiments, the kinetic parameters can relate to one or more of these three stages.

As used here "steady state signal" refers to a signal having an amplitude that exhibits a change of less than X % over a predetermined time period, wherein X is less than 25 or less than 20 or less than 15 or less than 10 or less than 5, and wherein the predetermined time period is at least 10% or at least 25% or at least 20% or at least 25% or at least 30% or at least 40% or at least 45% or at least 50% of a duration defined between a first time point at which the signal rises to a level above a first threshold, and a second time point at which the signal descents to a level below a second threshold. In some embodiments of the present invention the first threshold equals the second threshold. A typical duration defined between the first and second time points is from a few seconds to several minutes.

A representative example of a signal 120 that is generated by a sensing device of the explosive identification system of the present embodiments, and that manifests the aforementioned three-stage interaction process is illustrated in FIG. 12. The signal is illustrated as amplitude as a function of the time, and can indicate, for example, a change of an electrical property of the nanostructure or nanostructures that are employed by the sensing device. For example, the signal can indicate a change in the electrical conductance of the nanostructure or nanostructures of the sensing device. Such indication can be provided for example, by measuring the electrical current flowing through the nanostructure or nanostructures under constant applied voltage. Thus, in some embodiments of the present invention the signal is the current flowing through the nanostructure or nanostructures under constant applied voltage.

In FIG. 12, the first stage is the rise 122 of the signal, the second stage is the plateau 124, and the third stage is the descent 126 is the signal. Without wishing to be bound to any particular theory, it is assumed that the rise 122 describes a binding process of the explosive to the functional moiety, the plateau 124 is a manifestation of a thermodynamic equilibrium in the vicinity of the nanostructure or nanostructures of the sensor, and the descent 126 describes the unbinding process of the explosive off the functional moiety. Also shown in FIG. 12 is a threshold 128 that can be used according to some embodiments of the present invention to identify the onset of the rise 122 and the end of the descent 126 of signal 120. While FIG. 12 illustrates an embodiment in which the same threshold is used to identify both the onset of the rise and the end of the descent, this need not necessarily be the case, since the onset of the rise and the end of the descent can be identified using two different thresholds.

One or more of the three stages can be described by a coefficient which can serve according to some embodiments of the present invention as a kinetic parameter. Thus, a kinetic parameter can be selected from the group consisting of a characteristic binding coefficient, a characteristic unbinding coefficient, and a relation (such as, but not limited to, a ratio) between the characteristic binding coefficient and the characteristic unbinding coefficient.

In some embodiments of the present invention a characteristic binding coefficient is defined as the slope of the rise 122 of the signal, and characteristic unbinding coefficient is defined as the slope of the descent 126 of the signal.

Also contemplated is the use of at least one additional parameter. For example, in some embodiments of the present invention a parameter which describes the plateau 124 of the signal is employed. The additional parameter can be the average amplitude of signal 120 over the plateau 124, optionally and preferably a normalized average amplitude. In this embodiment, the parameter is non-kinetic since it describes the amplitude but does not include time-dependence information. Such a parameter can be viewed as a parameter that describes the thermodynamics of the interaction between the functional moiety.

Use of a kinetic parameter which describes the plateau of the signal is also contemplated. A representative example of such a parameter includes, without limitation, the aspect ratio of the area between the plateau and the time axis.

In some embodiments of the present invention at least one of the kinetic parameters is a relation between the slope v1 of the rise 122 of signal 120 before the plateau 124 and the slope v2 of the descent 126 of signal 120 after the plateau 124. For a single signal the relation can be, for example, a ratio between v1 and v2. When a plurality of signals are received from the same sensing device (for example, one signal from each nanostructure of the sensing device, wherein all the nanostructures of this sensing device have the same functional moiety attached thereto), the kinetic parameter(s) can describe a function that expresses the relation between v1 and v2, in a plane spanned by v1 and v2. For example, the kinetic parameter can be the parameter $\alpha$ in the relation $v2=\alpha v1+\beta$, where $\alpha$ and $\beta$ are two parameters that are extracted by fitting the pairs (v1, v2), as extracted from the plurality of signals of the same sensing device, to a straight line.

It was found by the present inventor that a single kinetic parameter is sufficient to describe the interaction of the explosive with a particular functional moiety for the purpose of constructing an explosive fingerprint. In experiments performed by the present inventors it was found that, for a given functional moiety and a given explosive, the relation between the slope v1 of the rise 122 of signal 120 before the plateau 124 and the slope v2 of the descent 126 of signal 120 after the plateau 124 is sufficient for describing the interaction between the functional moiety and the explosive.

Thus, in various exemplary embodiments of the invention the explosive fingerprint includes a plurality of parameters, respectively corresponding to a plurality of functional moieties, one parameter for each functional moiety, wherein each parameter is extracted from at least one signal (e.g., signal 120) generated responsively to an interaction of the explosive with the respective functional moiety, and wherein each parameter is defined as the relation between the slope of the rise of the at least one signal before the plateau and the slope of the descent of the at least one signal after the plateau.

The explosive fingerprint database of the present embodiments is typically stored as digital data in a searchable format in a computer readable medium. From the computer readable medium, one or more entries of the database can be pulled out and displayed on a display device. A database entry can be presented in more than one way. For example, the database entry can be presented as a text output specifying the classifier and the values of the parameters that define the fingerprint to which the classifier is associated. A database entry can alternatively be presented graphically. For example, the values of the parameters that define the fingerprint can be presented in the form of a chart, e.g., a column chart, a bar chart, a line chart, a pie chart.

Also contemplated are presentations in which each parameter value of a fingerprint is presented on a separate axis. A representative example of such presentation is illustrated in FIG. 13. Shown in FIG. 13 is a graphical presentation of a fingerprint defined over a set of six parameters. Each parameter is represented as an axis where all the axes share the same origin. The value of the parameter for the particular fingerprint is expressed by the distance from the origin over the respective axis, at which a mark (full circle, in the present example) is shown. In the representative example of FIG. 13 all the axes are drawn in the same plane, thereby forming a planar graph, but non-planar graphs in which at least three axes do not engage the same plane are also contemplated. Optionally and preferably, the presentation comprises a line that crosses each axis at a distance from the origin that corresponds to the value of the respective parameter, thus forming a radar chart. Preferably the line crosses each axis once. The crossing line can be closed or open. The radar chart can be used as a pattern the represents the fingerprint. These embodiments are particularly useful when a pattern matching is used for comparing two fingerprints.

FIG. 14 is a flowchart diagram describing a method suitable for identifying an explosive in a sample, according to some embodiments of the present invention.

Methods according to some embodiments of the present invention can be embodied in many forms. For example, a method can be embodied in on a tangible medium such as a computer for performing the method operations. It can be embodied on a computer readable medium, comprising non-volatile computer readable instructions for carrying out the method operations. In can also be embodied in electronic device having digital computer capabilities arranged to run the computer program on the tangible medium or execute the instruction on a computer readable medium.

The method begins at 140 and continues to 141 at which an explosive fingerprint Q of an unidentified explosive is received. The fingerprint Q is defined by a set of kinetic parameters, describing a plurality of interactions between the explosive and each of a respective plurality of functional moieties, as further detailed hereinabove.

The explosive fingerprint Q can be provided from any source. For example, in some embodiments of the present invention the fingerprint is transmitted to the method from a remote location, the fingerprint is transmitted to the method from a nearby location via a local communication line which can be wireless or wired, in some embodiments of the present invention the fingerprint is recorded on a computer readable medium from which the method receives the fingerprint, and in some embodiments of the present invention the fingerprint is constructed by the method from signals generated by sensing devices contacting the unidentified explosive, as further detailed hereinbelow.

The method continues to 142 at which a database of explosive fingerprints is accessed and searched for a database fingerprint matching the received fingerprint Q. The database of explosive fingerprints comprises a plurality of entries, where each entry j has a database explosive fingerprint $F_j$ and an explosive classifier $C_j$ associated with $F_j$, as further detailed hereinabove.

It will be appreciated that since the size of the fingerprints are relatively small, the search for a matching fingerprint is a simple and fast task. In particular, the database of present embodiments is superior to prior art techniques because according to a preferred embodiment of the present invention it is not necessary to subject the unidentified explosive to complicated laboratory tests such as electrochemistry, ion-mobility spectrometry, gas chromatography, HPLC, photoluminescence, surface acoustic-wave devices, microcantilevers, fluorescent polymers, surface plasmon resonance, quartz crystal microbalance and immunosensors.

Once the database fingerprint $F_j$ is found, the method continues to 143 at which the unidentified explosive is identified. Optionally and preferably the unidentified explosive is also identified by attributing the unidentified explosive with the explosive classifier $C_j$ which is associated with to the matched database fingerprint $F_j$. Once the explosive is identified the identification (e.g., the name or class of the explosive) can be transmitted 144 to a computer readable non-volatile medium, and/or displayed, e.g., on a display device or hardcopy, and/or transmitted over a communication network.

The method ends at 145.

An Exemplified Procedure for Constructing an Explosive Fingerprint:

FIG. 15 is a flowchart diagram illustrating a procedure suitable for constructing a fingerprint Q of an explosive in an explosive containing sample, according to some embodiments of the present invention. The procedure can be employed for executing operation 141.

The procedure analyzes signals received from a plurality of sensing devices, each sensing device employing one or more nanostructures, wherein each nanostructure has a functional moiety attached thereto, as defined hereinafter, and wherein for at least two sensing devices the functional moiety that is attached to the nanostructure or nanostructures of one of the sensing devices is different from the functional moiety that is attached to the nanostructure or nanostructures of the other sensing device. When the system comprises more than two sensing devices, for example, three sensing devices, either a different functional moiety that is attached to each of the nanostructure or nanostructures of each of the sensing devices, or one functional moiety is attached to the nanostructure or nanostructures of one of the sensing devices and a different functional moiety that is attached to the nanostructure or nanostructures of the other two sensing devices. Similarly, 2, 3, 4, 5, 6, 7, 8 or more functional moieties are attached to different sensing devices in the system, whereby each functional moiety can be attached to one or more sensing devices in the system. When a sensing device comprises a plurality of nano structures, at least some of the nano structures, e.g., all the nanostructures have the same functional moiety attached thereto, as further described hereinafter.

The following describes operations performed for one of the sensing devices. These operations are executed according to some embodiments of the present invention for each sensing device. This can be done sequentially, or, more preferably simultaneously.

The procedure begins at 150 and continues to 151 at which one or more signals are received from the respective sensing device in response to an interaction of the sensing device with the explosive. When the sensing device includes a plurality of nanostructures the procedure receives a signal from each of at least a portion of the plurality of nanostructures, e.g., from each of the plurality of nanostructures. The signal(s) is preferably indicative of an electric property of a nanostructure or nanostructures of the sensing device. For example, the signal(s) can represent current(s) flowing through the nanostructure or nanostructures, optionally and preferably under constant applied voltage. In these embodiments the signal(s) represent the conductance or resistance of the nanostructure or nanostructures.

The procedure optionally and preferably proceeds to 152 at which the signal(s) are normalize. When a plurality of signals is received from the respective sensing device, the normalization is optionally and preferably performed to establish overlap among at least a portion of the signals, e.g., among all the signals. This can be done by dividing the signal by a variation of the signal which is characteristic to the nanostructure itself. For example, in some embodiments of the present invention the nanostructure forms a transistor (e.g., a field-effect transistor) and the normalization comprises dividing the received signal by a gate-response that is characteristic to the nanostructure. A gate response can be calculated by measuring the variation in the source-drain current $I_{SD}$ responsively to a variation in the gate voltage $V_G$, and calculating the derivative of $I_{SD}$ with respect $V_G$.

The procedure proceeds to 153 at which one or more kinetic parameters is extracted from the signal or normalized signal. When a plurality of signals is received, the extraction 153 is preferably performed for each of at least a portion of the plurality of signals, e.g., for each of the plurality of signals. Preferably, at least one of the extracted parameters relates to the time-dependence of the signal. In an embodiment of the present invention, the procedure employs an algorithm that identifies three or more segments of the signal, wherein a first segment is a transition from a state in which the signal level is below a predetermined threshold, a second segment is characterized by a generally steady state signal, and a third segment is a transition from a generally steady state signal to a state in which the signal is below a predetermined threshold, as illustrated by segments 122, 124 and 126 of signal 120 (see FIG. 12). In some embodiments of the present invention, additional segments are also identified.

The identification of segments of the signal and the extraction of the parameter(s) from one or more of the identified segments can be done using any technique known in the art. For the identification of segments, the algorithm can employ a fitting algorithm so as to fit the signal to a predetermined shape or set of shapes. For example, the fitting algorithm can fit the signal to a piecewise-linear function or the like. In experiments performed by the present inventors, a Daubechies wavelet transform was employed to identify the rise and descent of the signal, but other types of transforms that employ a set of basis functions are also contemplated. Representative examples of sets of basis functions suitable for the present embodiments including, without limitation, half cosine functions, Legendre polynomials, polynomials, Haar wavelets, wavelets other than Haar wavelets and Daubechies wavelet, and sliding boxcar functions.

Once the segments are identified, the algorithm can extract one or more parameters that describe one or more of the segments. For example, the algorithm can identify a linear part of the first segment and a linear part of the third segment, and calculate the slopes of the identified linear parts, to provide a characteristic slope for each of the first and third segments. Each or both of these slopes can be used as the kinetic parameters. In some embodiments of the present invention the relation between the slope v1 that characterizes the first segment and the slope v2 that characterizes the second segment is calculated and used as a kinetic parameter.

When a plurality of signals are received, the slopes v1 and v2 are preferably extracted for each of at least a portion of the plurality of signals, e.g., for each of the plurality of signals, to provide a plurality of pairs (v1, v2). The relation between v1 and v2 can then be extracted by fitting the plurality of pairs (v1, v2) to a predetermined function, such as, but not limited to, a linear function. The kinetic parameter(s) can then be defined as one or more parameters that describe this function. For example, the pairs can be fitted to a linear function $v2 = \alpha \, v1 + \beta$, wherein $\alpha$ and $\beta$ are fitted parameters. In these embodiments the kinetic parameter is optionally and preferably the slope parameter $\alpha$.

Since the operations above are executed according to some embodiments of the present invention for each sensing device, the procedure provides a plurality of kinetic parameters, at least one kinetic parameter for each sensing device. The procedure continues to 154 at which an explosive fingerprint Q is defined as further detailed hereinabove using at least a portion of the kinetic parameters, e.g., all the kinetic parameters.

The procedure ends at 155.

FIG. 16 is a flowchart diagram illustrating a method suitable for identifying an unidentified explosive in an explosive containing sample, according to some embodiments of the present invention.

The method begins at 160 and continues to 161 at which the sample is contacted with a plurality of sensing devices, each containing one or more nanostructures, as further detailed hereinabove. The sensing devices are optionally and preferably all carried by the same substrate. The method continues to 162 at which the method determines an explosive fingerprint Q using the signals generated by the sensing devices in response to the interaction with the sample. This can be done, for example, by executing the procedure 150 described above.

The method continues to 142 at which a database of explosive fingerprints is accessed and searched for a database fingerprint matching the received fingerprint Q, as further detailed hereinabove. The method continues to 143 at which the presence of the unidentified explosive is determined, and optionally the identified, as further detailed hereinabove. Optionally and preferably the method continues to 144 at which the identification is transmitted to a computer readable non-volatile medium, and/or displayed, and/or transmitted over a communication network, as further detailed hereinabove.

In some optional embodiments of the present invention the method continues to 163 at which the sensing devices are washed to allow them to be used for analyzing another sample. The washing 163 can include flushing a washing solution pulse that restores the sensing devices to their initial baseline. Thus, the present embodiments provide multiuse sensing devices. In some embodiments of the present invention the same set of sensing devices is used for more than 10 or more than 100 cycles of sensing. Thus, in some embodiments, the method loops back to 161 wherein another sample is contacted with the sensing devices, one washed, and wherein the other operations are repeated for this sample.

The method ends at 164.

FIG. 17 is a flowchart diagram illustrating a method suitable for constructing a database of explosive fingerprints, according to some embodiments of the present invention.

The method begins at 170 and continues to 171 at which a previously identified explosive or a sample containing the previously identified explosive is contacted with a plurality of sensing devices, each containing one or more nanostructures, as further detailed hereinabove. The method continues to 172 at which the method determines an explosive fingerprint F using the signals generated by the sensing devices in response to the interaction with the sample. This can be done, for example, by executing the procedure 150 described above. The method continues to 173 at which the method defines a database entry which includes the explosive fingerprint F and an explosive classifier C, wherein the explosive classifier C comprises the identification (e.g., name, acronym) of the previously identified explosive.

The method continues to 174 at which the database entry is stored in a computer readable non-volatile medium. From 174 the method optionally and preferably proceeds to 163 at which the sensing devices are washed as further detailed hereinabove, and loops back to 171 at which another previously identified is analyzed. Each loop of the method thus generates a database entry, so that when a plurality of loops are executed, a database having a plurality of entries is formed. This database can be used by methods 140 and 160 above.

The method ends at 175.

An Exemplified System:

FIG. 18 is a schematic illustration of a system 180, according to some embodiments of the present invention. System 180 can be used for determining the presence of an explosive and optionally also identifying the explosive. System 180 comprises a substrate 182 deposited with a plurality of sensing devices 184, each sensing device comprising at least one semiconductor nanostructure 186 having attached thereto a functional moiety, selected to interact with an explosive. Nanostructures 186 are configured to generate a detectable signal responsively to the interaction with the explosive.

By "plurality" it is meant two or more sensing devices as described herein. Generally, system 180 is comprised of a substrate 182, where two or more regions of the substrate are configured as a sensing device. A region of the substrate that is configured as a sensing device having a plurality of nanostructures is interchangeably referred to herein as a sensing array. When system 180 comprises a plurality of sensing arrays, system 180 is interchangeably referred to herein as a multiarray.

In some embodiments, as system as described herein comprises two, three, four, five, six, seven eight or more sensing devices (sensing arrays). In some embodiments, a system as described herein can be referred to as comprising a plurality of nanostructures, divided into portions, wherein each portion of the nanostructures is as defined herein for a sensing device in the system.

As used herein, a "nanostructure" describes an elongated nanoscale semiconductor which, at any point along its length, has at least one cross-sectional dimension and, in some embodiments, two orthogonal cross-sectional dimensions less than 1 micron, or less than 500 nanometers, or less than 200 nanometers, or less than 150 nanometers, or less than 100 nanometers, or even less than 70, less than 50 nanometers, less than 20 nanometers, less than 10 nanometers, or less than 5 nanometers. In some embodiments, the cross-sectional dimension can be less than 2 nanometers or 1 nanometer.

In some embodiments, the nanostructure has at least one cross-sectional dimension ranging from 0.5 nanometers to 200 nanometers, or from 1 nm to 100 nm, or from 1 nm to 50 nm.

The length of a nanostructure expresses its elongation extent generally perpendicularly to its cross-section. According to some embodiments of the present invention the length of the nanostructure ranges from 10 nm to 50 microns.

The cross-section of the elongated semiconductor may have any arbitrary shape, including, but not limited to, circular, square, rectangular, elliptical and tubular. Regular and irregular shapes are included.

In various exemplary embodiments of the invention the nanostructure is a non-hollow structure, referred to herein as "nanowire".

A "wire" refers to any material having conductivity, namely having an ability to pass charge through itself.

In some embodiments, a nanowire has an average diameter that ranges from 0.5 nanometers to 200 nanometers, or from 1 nm to 100 nm, or from 1 nm to 50 nm.

In some embodiments of the present invention, the nanostructure is shaped as hollow tubes, preferably entirely hollow along their longitudinal axis, referred to herein as "nanotube" or as "nanotubular structure".

The nanotubes can be single-walled nanotubes, multi-walled nanotubes or a combination thereof.

In some embodiments, an average inner diameter of a nanotube ranges from 0.5 nanometers to 200 nanometers, or from 1 nm to 100 nm, or from 1 nm to 50 nm.

In case of multi-walled nanotubes, in some embodiments, an interwall distance can range from 0.5 nanometers to 200 nanometers, or from 1 nm to 100 nm, or from 1 nm to 50 nm.

Selection of suitable semiconductor materials for forming a nanostructure as described herein will be apparent and readily reproducible by those of ordinary skill in the art, in view of the guidelines provided herein for beneficially practicing embodiments of the invention. For example, the nanostructure of the present embodiments can be made of an elemental semiconductor of Group IV, and various combinations of two or more elements from any of Groups II, III, IV, V and VI of the periodic table of the elements.

As used herein, the term "Group" is given its usual definition as understood by one of ordinary skill in the art. For instance, Group III elements include B, Al, Ga, In and Tl; Group IV elements include C, Si, Ge, Sn and Pb; Group V elements include N, P, As, Sb and Bi; and Group VI elements include O, S, Se, Te and Po.

In some embodiments of the present invention the nanostructure is made of a semiconductor material that is doped with donor atoms, known as "dopant". The present embodiments contemplate doping to effect both n-type (an excess of electrons than what completes a lattice structure lattice structure) and p-type (a deficit of electrons than what completes a lattice structure) doping. The extra electrons in the n-type material or the holes (deficit of electrons) left in the p-type material serve as negative and positive charge carriers, respectively. Donor atoms suitable as p-type dopants and as n-type dopants are known in the art.

For example, the nanostructure can be made from silicon doped with, e.g., B (typically, but not necessarily Diborane), Ga or Al, to provide a p-type semiconductor nanostructure, or with P (typically, but not necessarily Phosphine), As or Sb or to provide an n-type semiconductor nanostructure.

In experiments performed by the present inventors, Si nanowires and p-type Si nanowires with a diborane dopant have been utilized.

In some embodiments, the nanostructures 186 are grown on substrate 182 by using, for example, chemical vapor deposition. Optionally, once the nanowires and/or nanotubes are obtained, the substrate is etched (e.g., by photolithography) and the nanowires and/or nanotubes are arranged within the sensing device as desired. Alternatively, nanowires can be made using laser assisted catalytic growth (LCG). Any method for forming a semiconductor nanostructure and of constructing an array of a plurality of nanostructures as described herein is contemplated.

In some embodiments, at least one of sensing devices 184 of system 180 comprises at least 2 or at least 4 or at least 8 or at least 16 nanostructures. Preferably, but not necessarily, all the nanostructures of the sensing device occupy an area which is less than 1 square centimeter. The nanostructures can comprise nanowires, as described herein, nanotubes, as described herein, and combination thereof.

Exemplary nanotubes and methods of preparing same are disclosed in WO 2010/052704, which is incorporated by reference as if fully set forth herein.

Any other semiconductor nanostructures are also contemplated.

The functional moiety is selected to interact with an explosive and is configured such that a detectable signal responsively to this interaction is generated. That is, the functional moiety is attached to the nanostructure in such a way that upon interaction with an explosive, a change occurs in a property of the nanostructure, and this change is a detectable change.

For example, the nanostructure can exhibit a change in density of electrons or holes over some region of the nanostructure or over the entire length of nanostructure. The nanostructure can exhibit a change in its conductance and resistance.

The change in the property of nanostructures 186 can be detected by a detector 188 which communicates with each or at least some of nanostructure 186 via a communication line 190. For clarity of presentation only one communication channel 190 is illustrated in FIG. 18. However, the present embodiments contemplate a configuration in which more than one nanostructure (e.g., each nanostructures) is separately connected to detector 188 via a separate communication channel. One of ordinary skills in the art, provided with the details described herein would know how to adjust FIG. 18 for a configuration in which more than one nanostructure is connected to detector 188. An exemplified configuration with a plurality of individual communication channels is described in the Examples section that follows, see, for example, FIG. 6.

Detector 188 can be of any type that allows detection of semiconductor property.

For example, detector 188 can be constructed for measuring a change in electrical properties such as, for example, voltage, current, conductance, resistance, impedance, inductance, charge, etc.

The detector typically includes a power source for applying voltage to the nanostructure and a voltmeter or amperemeter. In one embodiment, a conductance less than 1 nS is detected. In some embodiments, a conductance in the range of thousands of nS is detected.

For example, when a molecule of the explosive effects a change in electron or hole density of nanostructure 186, detector 188 can be configured to apply voltage to nanostructure 186 and to measure the current through nanostructure 186. In some embodiments of the present invention nanostructure 186 is in contact with a source electrode and a drain electrode (not shown, see FIG. 19). In these embodiments, detector 188 is optionally and preferably configured to apply a source-drain voltage between the source electrode and the drain electrode and to measure changes in the source-drain current. In some embodiments of the present invention nanostructure 186 is in contact with a source electrode, a drain electrode and a gate electrode, such that nanostructure 186 forms a transistor, such as, but not limited to, a field effect transistor (FET). In these embodiments, detector 188 is optionally and preferably configured to apply a source-drain voltage between the source electrode and the drain electrode and optionally also a gate voltage to the gate electrode, and to measure changes in the source-drain current.

FIG. 19 is a schematic illustration of nanostructure 186 in embodiment in which nanostructure 186 forms a transistor 200 (e.g., FET). Transistor 200 comprises a source electrode 202, a drain electrode 204, and a gate electrode 206 wherein nanostructure 186 serves as a channel. A gate voltage can be applied to channel nanostructure 186 through gate electrode 206. In some embodiments, when the voltage of gate electrode 206 is zero, nanostructure 186 does not contain any free charge carriers and is essentially an insulator. As the gate voltage is increased, the electric field caused thereby attracts electrons (or more generally, charge carriers) from source electrode 202 and drain electrode 204, and nanostructure 186 becomes conducting. In some embodiments, no gate voltage is applied and the change in the charge carrier density is effected solely by virtue of the interaction between nanostructure 186 and the molecule of the explosive.

It is appreciated that when the electrical property of the nanostructure varies in response to interaction with a sample that contains the explosive, a detectable signal is produced. For example, a change in the electrical property induces a change in the characteristic response of the transistor to the gate voltage (e.g., the source-drain current as a function of the gate voltage), which change can be detected and analyzed.

Detector 188 optionally and preferably communicates with a signal processor 192, which is configured for receiving and analyzing the detected signals. To allow processor to receive more than one signal simultaneously, the communication channel to signal processor 192 is preferably a multiplexed channel. For example, a plurality of communication lines can connect detector 188 and processor 192. In some embodiments of the present invention signal processor 192 is a signal processing system that also has detection capabilities, in which case it is not necessary for system 180 to include a separate detector.

Signal processor 192 can have a dedicated circuit configured to perform the analysis of the signals. Signal processor 192 can be an analog signal processor or a digital signal processor. In some embodiments of the present invention signal processor 192 is a data processor such as a computer configured for receiving and analyzing the signals. Signal processor 192 extracts, from each generated signal, a kinetic parameter describing a respective interaction of the sample with a respective sensing device 184. The extracted set of kinetic parameters define an explosive fingerprint, as further detailed hereinabove, and therefore signal processor 192 constructs an explosive fingerprint. In various exemplary embodiments of the invention processor 192 is configured to execute one or more operations (e.g., all the operations) of method 140 and/or method 150. In various exemplary embodiments of the invention processor 192 is configured to construct a fingerprint database, as further detailed hereinabove. In these embodiments, processor 192 is configured to construct at least one of operations 172-174 (e.g., each of operations 172-174) of method 170.

System 180 optionally and preferably comprises a plurality of fluid channels 194, arranged to allow fluidic sample to flow into each individual sensing device 184. In some embodiments of the present invention there is a fluid communication among all the fluid channels 194, so as to allow them to transmit different portions of the same sample to each of sensing devices 184. In some embodiments of the present invention at least one of fluid channel 194 is separated from any other fluid channel, thereby allowing transmitting different samples separately into different sensing devices.

In the embodiment illustrated fluid channels 194 are shown as a main channel that is connected to an input port 196. The main channel branches into secondary channels so that each sensing device 184 fluidly communicates with the main channel via a secondary channel. However, this need not necessarily be the case, since, for some applications, it may not be necessary for the system to include a main channel and a plurality of secondary channel. For example, all channels can connect the sensing devices directly to the input port. Channels 194 can be close or open and can have any size. In some embodiments of the present invention the channels have a diameter which is above 1 mm, and in some embodiments the channels are microchannels having a diameter from about 1 µm to about 1 mm Embodiments in which both channels above 1 mm in diameter and channels below 1 mm in diameter are employed, are also contemplated.

Also contemplated are embodiments in which the sample is transferred to the sensing devices directly without fluid channels. For example, the sensing devices can be made open to the environment, e.g., from above, so that the analyzed sample is the environment near (e.g., above) system 180.

Fluid channels 194 can also be used for washing the sensing devices from traces of previously analyzed samples. Alternatively, system 180 can comprise a separate arrangement of fluid channels (not shown), wherein, in operation, fluid channels 194 are used for transmitting the sample to the sensing devices and the separate arrangement of fluid channels is used for washing the sensing devices and optionally also channels 194.

Herein throughout, in some embodiments, a system as described herein can be interchangeably presented as comprising a substrate and a plurality of semiconducting nanostructures deposited onto the substrate, wherein the plurality of nanostructures comprises at least two portions of differently-modified nanostructures, as described herein. Herein throughout, differently-modified nanostructures are such that at least two of the portions of nanostructures in the device comprise nanostructures having attached thereto a different functional moiety, as described herein. Upon contacting an explosive-containing sample with the device, the plurality of nanostructures exhibits a set of detectable signals as described herein, which represent a set of detectable changes in an electrical property of each portion in the plurality of nanostructures. The set of detectable changes represents a set of different interactions of each functional moiety with an explosive.

In some embodiments, the system comprises two, three, four, five, six, seven, eight or more portions of differently-modified nanostructures.

In some embodiments, the comprises two or more portions of differently modified nanostructures, and the set of detectable changes represents a set of changes in a kinetic parameter, as described herein.

The Functional Moiety:

As noted herein, a functional moiety is attached to the nanostructure and is configured so as to generate a detectable signal, as described herein, upon interaction with an explosive.

In some embodiments, the functional moiety is configured to interact with an explosive by forming a complex with the explosive.

A "complex", as used herein, describes a form in which two or more chemical entities are in association with one another. The association can involve a partial transfer of electronic charge, a partial sharing of electrons, hydrogen bond interactions, Van der Waals forces and/or "inclusion" association (via a clathrate).

The complex can be, for example, a charge transfer complex, an inclusion complex (a host-guest complex; a clathrate), a coordination complex.

As defined in IUPAC, a "charge-transfer complex" is an electron-donor-electron-acceptor complex, characterized by electronic transition(s) to an excited state in which there is a partial transfer of electronic charge from the donor to the acceptor moiety.

An inclusion complex or a host-guest complex is a complex in which one component (the host) forms a cavity or space(s) in which molecular entities of a second chemical species (the guest) are located. There is no covalent bonding between guest and host, the attraction being typically due to van der Waals forces but can also involve charge transfer interactions.

A coordination complex is typically an organometallic complex in which ligands are in association with a central metal atom or atoms.

According to some of the present embodiments, a functional moiety is configured to interact with an explosive by forming a complex with the explosive, whereby this complex formation leads to a change in the electronic structure (e.g., a change in electron density, conductance, resistance) of the nanostructure, as defined hereinabove, and to a detectable signal.

For example, when a functional moiety forms a charge transfer complex with an explosive, a change in the electron density on the surface of the nanostructure occurs.

In another example, when a functional moiety forms an inclusion complex with an electron-rich explosive, the presence of the electron-rich explosive in proximity to the nanostructure leads to a change in the electron density on the nanostructure.

In another example, when a functional moiety forms a coordination complex, a change in electron density occurs.

In some embodiments, a length of the functional moiety is smaller than 2 nm, smaller than 1.5 nm, and even smaller than 1 nm. This allows the formation of the complex to occur close to the nanostructures' surface, thereby enhancing the device's sensitivity.

In some of any one of the embodiments described herein, the functional moiety is configured to interact with an explosive by forming a charge transfer complex with the explosive.

In these embodiments, an electron-deficient (or electron withdrawing) functional moiety forms a charge transfer complex with an electron-rich explosive, and vice vera, an electron-rich (or electron-donating) functional moiety forms a charge transfer complex with an electron-deficient explosive.

In exemplary embodiments, a functional moiety is configured to form a charge transfer complex with a nitro-containing explosive, and with any other electron deficient explosive.

Since the nitro group in nitro-containing compounds acts as an electron-withdrawing group, nitro-containing compounds typically comprise domains which exhibit a partial positive charge, due to electron resonance between these domains and the nitro group(s).

In some embodiments, a functional moiety is an electron donating moiety.

Without being bound by any particular theory, it is assumed that the electron donating moiety forms a charge transfer complex with the positively charged domains in the nitro-containing compounds.

Thus, in some embodiments, in a charge-transfer complex as described herein, the electron donor in an electron-donating functional moiety attached to the nanostructure by means of a modified nanostructure, as described herein, and the electron-acceptor is the nitro-containing moiety.

As used herein, the phrase "electron donating" with respect to a moiety or group describes a moiety or group that comprises at least one electron donating atom, as this phrase is defined herein.

As used herein, the phrase "electron donating atom" describes any atom in a chemical group or moiety which is capable of donating one or more electrons to an electron acceptor (e.g., an atom or a molecule that exhibits electron deficiency), so as to interact with the acceptor (e.g., via formation of a charge transfer complex). Typically, the electron donating atom is characterized by the presence of a free electron pair. Various heteroatoms (e.g., phosphorus, sulfur, nitrogen, oxygen) are known in the art to be capable of acting as electron donating atoms. In addition, a carbon atom in an N-heterocyclic carbene (e.g., an N-heterocyclic carbene which is a five- or six-membered heteroalicyclic or heteroaromatic ring described herein) may be a suitable electron donating atom.

In some of these embodiments, the functional moiety is selected such that a Debye length of at least 100 nm, at least 500 nm, at least 800 nm and even 1 micron and higher is exhibited.

As used herein and in the art, the phrase "Debye length" describes the distance over which significant charge separation can occur.

Without being bound by any particular theory, such Debye length value result in reduced shielding of the charge transfer, which may stem from formation of a charge-transfer complex in close proximity to the nanostructure (e.g., by using a functional moiety with a length as described herein).

Exemplary functional moieties include, but are not limited to, alkyl, alkenyl, alkynyl, aryl and cycloalkyl, each being substituted by one or more electron donating group(s), and each being smaller than 2 nm in length, smaller than 1.5 nm, and even smaller than 1 nm.

In some embodiments, the functional moiety is an alkyl, alkenyl or alkynyl, being from 1 to 10 carbon atoms in length, and being substituted by one or more electron donating moieties.

In some embodiments, the alkyl, alkenyl or alkynyl described herein is being of from 1 to 9 carbon atoms, or from 1 to 8 carbon atoms, or from 1 to 7 carbon atoms, or from 1 to 6 carbon atoms, or from 1 to 5 carbon atoms, or from 1 to 5 carbon atoms, or from 1 to 4 carbon atoms, or from 1 to 3 carbon atoms, or from 1 to 2 carbon atoms in length, or of 1 carbon atom in length.

In some embodiments, alkyl, alkenyl or alkynyl described herein is being from 1 to 4 carbon atoms in length.

In some embodiments, the functional moiety is an alkyl being from 1 to 4 carbon atoms in length and comprising one or more electron-donating moieties.

The electron-donating moieties are preferably located at the distal terminus of the alkyl, alkenyl or alkynyl, with respect to the nanostructure's surface, so as to be exposed to interacting with e.g., a nitro-containing compound.

In some embodiments, the functional moiety is a cyclic moiety, such as aryl or cycloalkyl, being smaller than 2 mm in length and hence being formed of from 1 to 3 fused rings, and comprising one or more electron-donating group as substituent(s). The substituent is preferably located so as to be exposed to interacting with the explosive (e.g., a nitro-containing explosive).

In some embodiments, the functional moiety is selected from the group consisting of a heteroalicyclic and a heteroaryl, each comprising a heteroatom that functions as an electron donating group.

In some embodiments, the heteroatom is nitrogen, being substituted or unsubstituted. In cases where the nitrogen atom is substituted, the substituent is preferably such that enhances its electron donating properties, namely, is a substituent which features an electron inductive effect (e.g., alkyls), yet do not impart steric hindrance (e.g., lower alkyl such as methyl or ethyl).

Exemplary electron donating groups include, but are not limited to, amine, thiol, pyrrole, alkoxy, thioalkoxy, aryloxy and thioaryloxy.

In some embodiments, the electron donating group is amine, as defined herein.

The amine can be unsubstituted or substituted, namely, be a primary amine or a secondary amine, as defined herein. In cases where the amine is substituted, the substituent(s) are preferably such that enhance its electron donating properties, namely, are substituents which feature an electron inductive effect (e.g., alkyls), yet do not impart steric hindrance (e.g., lower alkyl such as methyl or ethyl).

In some embodiments, the functional moiety is an amino-alkyl, the alkyl being 1-10 carbon atoms in length.

In some embodiments, the alkyl is being 1-5 carbon atoms in length.

In some embodiments, the functional moiety is aminopropyl.

In some embodiments, the functional moiety is N-methylaminopropyl.

In some embodiments, the functional moiety is a pyrroloalkyl, e.g., n-alkyl-1H-pyrrole, the alkyl being 1-10 carbon atoms in length.

In some of these embodiments, the alkyl is being 1-5 carbon atoms in length.

Other suitable functional moieties include, but are not limited to, aminoaryl (an aryl substituted by an amine such as aniline), an alkoxyarylamine, an alkylarylamine, calyx[n]pyrrole, with n being e.g., from 3 to 6.

It is noted that for an aminoaryl, for example, substituents that feature an inductive effect so as to enhance the electron donating property of the amine are beneficial, and result in increased interaction with an electron-deficient explosive. Thus, substituents such as aryloxy or alkyl, when positioned at the ortho or para position with respect to the amine are preferred.

It is to be further noted that explosives (e.g., nitro-containing compounds) which exhibit lower electron deficiency (e.g., aromatic compounds with a plurality of nitro or other electron withdrawing substituents) exhibit stronger interaction with electron donating functional moiety, compared to compounds that are less electron deficient (e.g., with one nitro substituent or which are aliphatic compounds). Similarly, stronger interactions are exhibited for functional groups that exhibit stronger electron donating property. Thus, a functional moiety exhibits different interactions with explosives with different levels of electron-deficiency, and functional moieties with different electron donating properties exhibit different interactions with a certain explosive.

The level of interaction (the binding strength and corresponding binding and unbinding coefficients) between the functional moiety and the explosive is reflected, for example, by a kinetic parameter of the interaction, as defined herein.

Such sets of interactions are utilized accordingly, in some embodiments of the present invention, as defined herein.

For example, while TNT exhibits a high extent of electron deficiency, compounds with less nitro substituents or aliphatic nitro-containing compounds interact weakly with a functional group such as, for example, aminopropyl functional group, yet, such compounds interact stronger with stronger functional moieties such as, for example, N-methylpropylamine or 2-methoxyaniline.

In some embodiments, a functional group is configured to interact with an explosive by forming an inclusion complex.

Such functional moieties are suitable, for example, to form a complex with explosives which are cyclic and may act as a host in such complexes. Alternatively, such functional moieties can function as a host, and form a complex with a suitable guest. Criteria for forming a host-guest complex and thereby for selecting a functional group that may interact by forming inclusion complex with one or more explosives should be recognized by those skilled in the art.

Exemplary pairs for forming host-guest complexes are molecularly imprinted polymers, which may serve as functional groups designed so as to form an inclusion complex with a target explosive.

An exemplary such functional group is a metal oxide particle. The strength of interaction with an explosive by formation of an inclusion complex depends, inter alia, on the size and geometry suitability of the metal ions in the oxide particles and the explosive. Thus, a functional group which comprises metal oxide particles of different metal ions interacts differently with cyclic explosives which have a different cavity size. Similarly, a cyclic explosive interacts differently with metal oxide particles of different sizes of the metal ion. The different interaction levels as described herein generate a set of interactions that are utilized by the different embodiments of the present invention.

In some embodiments, the metal oxide particles have an average particle size that ranges from 1 nm to 100 nm, or from 1 nm to 50 nm, including any subrange and any value therebetween. Exemplary metal oxide particles have an average size of from about 1 nm to about 20 nm.

The size of the particles may affect sensitivity, as described herein for a functional moiety, and is accordingly selected as desired.

It is to be noted that a functional moiety that comprises metal oxide particles may also participate in formation of a charge transfer complex and/or a coordination complex, since metal oxide particles typically comprise an electron deficient center (a positively-charged metal) and electron-donating oxygen atoms. Such a functional moiety can therefore interact also with explosives that do not form therewith an inclusion complex. Such a functional moiety also exhibits different levels of interaction (different binding strengths) with explosives exhibiting various levels of electron deficiency or electron donation.

In some embodiments, a functional moiety that comprises metal oxide particles is suitable for interacting with a peroxide-containing explosive, as described herein, preferably cyclic peroxide-containing explosives, and optionally also for interacting with some nitro-containing explosives.

Metal oxide particles that are suitable for interacting with e.g., cyclic peroxide-containing explosives include, but are not limited to, particles (e.g., nanoparticles) of an oxide of a metal such as zinc, lithium, copper, cadmium, indium, titanium, Sb and Sc. Any oxide of these metals is contemplated. Some non-limiting guidance for selecting a metal oxide are provided in Dubnikova et al. (2002), supra.

A functional group as described herein can be attached to the nanostructure covalently or non-covalently.

When attached covalently, the functional moiety forms a covalent bond with one or more reactive groups of the nanostructure. When attached non-covalently, the functional moiety can be attached to the nanostructure via non-covalent chemical interactions such as, for example, electrostatic interactions, aromatic interactions, coordination interactions, hydrogen bond interactions and the like, or by physical interactions, for example, by being deposited on the surface of nanostructure.

Preferably, the functional group forms a covalent or non-covalent bond with one or more surface reactive group(s) of the nanostructure, such that the nanostructure having a functional moiety attached thereto is a surface-modified nanostructure.

In some embodiments, the functional moiety is covalently attached to the nanostructure's surface by means of covalent bonds formed between reactive groups within the functional moiety and compatible reactive groups on the surface of the nanostructures.

Reactive groups on the nanostructure's surface are either intrinsic or can be generated upon a suitable treatment. In some embodiments, where the nanostructure is SiNW or silicon nanotubes, free hydroxyl groups are intrinsically present on the surface of the nanostructures and can be utilized for covalently attaching functional moieties thereto.

Alternatively, the nanostructures described herein are first surface-modified so as to generate surface reactive groups. Such a surface modification can be performed by, for example, attaching to intrinsic functional groups on the surface a bifunctional linker molecule, which comprises in one terminus thereof a reactive group that is capable of attaching (covalently or non-covalently) to these intrinsic functional groups and in another terminus thereof a reactive group that can attach (covalently or non-covalently) to the functional moiety.

In some embodiments, the functional moiety comprises, prior to being attached to the nanostructure, a reactive group that can react with a reactive group on the nanostructure surface so as to form a covalent bond with the surface.

Selecting reactive groups that are compatible with functional groups on the nanostructure of choice is within the capabilities of a person skilled in the art, particularly in view of the guidance provided herein.

In some embodiments, when the nanostructure is SiNW or silicon nanotubes, the functional moiety comprises a reactive group capable of forming covalent bond with free hydroxy groups on the nanostructure surface. Exemplary such reactive groups include, but are not limited to, halides and alkoxides, which can act as leaving groups so as to form an ether bond, carboxylic acids or esters, which can form an ester bond via esterification or trans esterfication, as well as halosilanes and orthosilicates, which can form —Si—O— bonds.

According to some embodiments of the invention, the functional moiety is attached to the nanostructure via any one of the covalent bonds described herein.

In some embodiments, the functional moiety is an aminoalkyl and the aminoalkly is derived from an aminoalkyltriorthsilicate, such as, for example, aminopropyltriorthosilicate or N-methylaminopropylorthosilicate, or from aminoalkyl dialkylalkoxysilane.

In some embodiments, the functional moiety is an aminoalkyl or an aminoaryl, and the aminoalkyl or aminoaryl is derived from aminoalkyl that is further substituted by halide or aminoaryl substituted by haloalkyl or aminoaryl substituted by triorthosilicate or by dialkylalkoxysilane.

Other bifunctional compounds which comprise a functional moiety as described herein and a reactive group suitable for forming a covalent with a nanostructure as described herein, are contemplated.

Exemplary silane derivatives that are suitable for generating functional moieties that are covalently attached to a Si nanostructure are presented in FIGS. 1A-E. Exemplary corresponding functional moieties covalently attached to Si nanostructures are presented in FIG. 6.

In some embodiments, the functional moiety is non-covalently attached to a nanostructure. Such functional moieties can be attached to the nanostructure by means of, for example, deposition, e.g., by means of generating the functional moiety in situ under conditions suitable for generating a functional moiety on the nanostructure's surface. Optionally, such functional moieties can be attached to the nanostructure by means of coordination complexes, electrostatic interactions, and any other chemical, non-covalent interaction as described herein.

In some embodiments, when the functional moiety comprises metal oxide particles, such particles can be generated from corresponding metal particles by means of atomic layer deposition (ALD) which allows finely controlling the particles' size.

In some embodiments, when the functional moiety comprises metal oxide particles, these particles are attached to the nanostructure by means of ALD from a corresponding metal and under suitable reaction conditions. Without being bound by any particular theory, it is assumed that the metal oxide particles are attached to Si-nanostructures by interacting with intrinsic hydroxy surface groups of such nanostructures.

A system as described herein comprises two or more sensing devices, and the functional moieties of at least two of the sensing devices are different from one another.

In some embodiments, 2, 3, 4, 5, 6, 7, 8 or more different functional moieties are comprised in each system, namely, are attached to nanostructures in the sensing devices of a system. In some of these embodiments, each sensing device in the system comprises nanostructures having attached thereto a different functional moiety. In some embodiments, at least two sensing devices comprise nanostructures having attached thereto the same functional moiety.

In any one of the embodiments described herein, for each sensing device that comprises more than one nanostructure, at least 10%, at least 20%, at least 30%, at least 40%, preferably at least 50%, at least 60%, at least 70%, at least 80%, at least 90% or at least 100% of the nanostructures have the functional moiety attached thereto.

In any one of the systems described herein, and in any one of the embodiments thereof, various combinations of any one of functional moieties described herein can be employed in the sensing devices.

It is to be noted that embodiments of the present invention also encompass nanostructures which have a functional moiety attached thereto intrinsically, and these nanostructures are used without further modifying the functionality of their surface, and are considered herein as having a functional moiety configured to interact with an explosive as described herein.

It is to be further noted that embodiments of the present invention also encompass system in which one or more sensing devices do not have a functional moiety as described herein attached thereto. Such nanostructures can be nanostructures which have not been modified to include a functional moiety as described herein or which have been modified to block an interaction between intrinsic functional moieties of the nanostructure and an explosive.

Herein throughout, an "explosive" describes a highly energetic, chemically-unstable compound having a rapid rate of autodecomposition. The term explosive, as used herein also encompasses fragments of the compound, which optionally but not necessarily exhibit the above-indicated properties of the explosive, and also encompasses a mixture of compounds and/or of fragments which exhibits the above indicated properties of an explosive.

The term "explosive" encompasses generally an explosive material, yet also encompasses an explosive residue (e.g., a substance obtained upon explosion) and a material associated with an explosive material (e.g., a starting material for preparing an explosive material).

Exemplary explosives include, but are not limited to, nitro-containing compounds, such as, for example, nitroaromatic-based explosives, nitramine-based explosives, nitrate ester-based explosives, and inorganic nitrate-based explosives; chlorate-based explosives, perchlorate-based explosives; bromate-based explosives; peroxide-based explosives; smokeless powder-based explosives and black-powder-based explosives.

As used herein, the phrase "nitro-containing compound" encompasses compounds which include one or more nitro groups, attached to, for example, saturated or unsaturated, linear or cyclic, hydrocarbon backbone.

A nitro-containing compound can therefore be comprised of an aliphatic or alicyclic or aromatic hydrocarbon moiety, substituted by one or more nitro groups. The hydrocarbon moiety can optionally be interrupted by one or more heteroatoms such as nitrogen, oxygen, sulfur, phosphor, silicon, boron.

In some embodiments, the nitro-containing compound comprises an aromatic moiety (e.g., an aryl) substituted by one or more nitro groups, and is also referred to herein and in the art as nitroaromatic-based explosive. E.g., TNT.

Nitro-containing compounds which comprise a cyclic, non aromatic carbon, which comprise a nitramine moiety (a nitro group attached to an amine) are also referred to herein as nitramine-based explosive. E.g., HMX, RDX.

Nitrate ester-based explosives are aliphatic, alicyclic or aromatic compounds substituted by or more nitrate ester groups. E.g., PETN, NG.

Inorganic nitrate-based explosives include, for example, salts having one or more nitrate ion groups. E.g., ammonia nitrate.

In some embodiments, the nitro-containing compound is an explosive.

Exemplary nitro-containing compounds which can be detected by utilizing the methods, devices and systems described herein include, but are not limited to, 2-nitrotoluene; 3-nitrotoluene; 4-nitrotoluene; 2,4,6-trinitrotoluene (TNT); 2,4-dinitrotoluene; 3,4-dinitrotoluene; 2,6-dinitrotoluene; ethylene glycol dinitrate (EGDN); nitroglycerine (NG); nitrocellulose; ammonium nitrate, cyclotrimethylenetrinitramine (cyclonite; RDX); pentaerythritol tetranitrate (PETN); homocyclonite (octogen; HMX); 2,4,6-Trinitrophenylmethylnitramine (Tetryl); picric acid; 1,2,3-propanetrial trinitrate and any mixture and/or formulation thereof, including, for example, 1,2,3-propanetrial trinitrate Formulations (e.g., NitroBid); C-2 (RDX, TNT, DNT and NG); C-3 (RDX, TNT, DNT, Tetryl and NG); C-4 (RDX and PETN), Semtex (RDX and PETN); Detasheet (RDX and PETN); Dynamites (EDGN and NG); Pentolite (PETN+TNT); PTX-1 (RDX, TNT and Tetryl); PTX-2 (RDX, TNT and PETN); and Tetryol (TNT and Tetryl). Some exemplary nitro-containing compounds are presented in FIGS. 1C and 1D.

A peroxide-containing compound is used herein to describe organic and inorganic compounds that include one or more peroxides [—O—O—]. The compound can be comprised of an aliphatic or alicyclic or aromatic hydrocarbon moiety, substituted by one or more peroxide-containing groups such as, for example, O—OR groups, with R being alkyl, cycloalkyl, aryl, hydrogen and the like. The hydrocarbon moiety can optionally be interrupted by one or more heteroatoms, as described herein. Alternatively, or in addition, the compound can be comprised of a hydrocarbon (e.g., aliphatic or alicyclic) interrupted by one or peroxide groups.

Peroxide-containing explosives are typically cyclic compounds, which include one or more peroxides interrupting the cyclic hydrocarbon, and may optionally be substituted and/or include additional interrupting heteroatoms. Examples include, but are not limited to, TATP, HMDT and TMDD (see, FIG. 1E).

Linear peroxide-containing explosives are also contemplated, as well as inorganic peroxide-containing compounds or compounds capable of generating peroxide-containing compounds.

Peroxide-containing compounds also encompass hydrogen peroxide, which is often used to construct explosives.

Other explosives would be readily recognized by persons skilled in the art.

For any one of the embodiments described herein, the sample encompasses samples suspected as containing an explosive, such that the systems and methods described herein are utilized for determining a presence and optionally an amount of an explosive and further optionally an identity (e.g., the chemical composition) of an explosive. Optionally, the sample is known to contain an explosive and the methods and systems described herein are utilized for determining an amount and/or identity of the explosive in the sample.

For any of the embodiments described herein, the methods and systems described herein can be used for identifying a presence or absence of an explosive as described herein, and can be efficiently utilized for discriminating explosives from chemically-related non-explosive compounds or mixtures of compounds.

For example, when a sample is suspected as containing a compound which is an explosive, the methods and systems described herein can be used to determine if the compound is an explosive or a chemically-related non-explosive compound.

A database of explosive fingerprints as described herein, can be used according to some embodiments of the invention for determining whether or not a compound in a tested sample contains an explosive. For example, a fingerprint Q of the tested sample can be determined as described herein and the database can be searched for a similar database fingerprint. If the database does not contain any database fingerprint that is similar to the fingerprint Q, then the tested sample can be declared as being free of explosives, or, more preferably, free of any explosive that has an entry in the database. If the database contains a database fingerprint $F_j$ that is similar to Q, then the tested sample can be declared as containing the explosive that corresponds to the respective classifier $C_j$.

In some embodiments, the sample is a fluid sample, and can be a liquid sample or a gaseous sample.

In some embodiments, the sample is air.

Fluid samples are contacted with a system as described herein by, for example, contacting the sample, or a solution comprising a dissolved liquid or gaseous sample, with the nanostructures.

In some embodiments, the sample is a solid sample, for example, solid particles or a powder.

Solid samples are contacted with a system as described herein by, for example, contacting a solution comprising a dissolved sample, with the nanostructures.

For any one of the embodiments described herein, the explosive is in a fluid state (e.g., is in a liquid state or a gaseous state) or in a solid state (e.g., solid particles or powder).

The term "fluid" is defined as a substance that tends to flow and to conform to the outline of its container. Typical fluids include liquids and gasses, but may also include free flowing solid particles.

In some embodiments, the explosive is in a gaseous state.

By "gaseous state" it is meant that at least a portion of the compound is in a form of vapors. Thus, for example, the compound can be a liquid or a solid at room temperature, yet, it is volatile to some extent, such that a portion thereof is in a gaseous state at room temperature. Alternatively, the compound can be in such a gaseous state upon heating a sample containing same.

Since, as noted herein, the method described herein can be utilized for detecting ultra-low amounts (traces) of explosives, the portion of a compound in a gaseous state can be ultra-law, as is further detailed hereinbelow.

In some embodiments, a concentration of the explosive in the sample is lower than 1 micromolar, lower than 1 nanomolar, lower than 1 picomolar, lower than 1 femtomolar and even is at the attomolar range.

In some embodiments, a concentration of the explosive in the sample ranges from 1 micromolar to 1 attomolar, or from 1 microliter to 1 nanomolar, or from 1 microliter to 1 picomolar, or from 1 micromolar to 1 femtomolar, or from 1 nanomolar to 1 picomolar, or from 1 nanomolar to 1 femtomolar, or from 1 nanomolar to 1 attomolar, or from 1 picomolar to 1 femtomolar, or from 1 picomolar to 1 attomolar, or from 1 femtomolar to attomolar.

The concentration of the explosive encompasses a concentration of the compound's vapors in air or other gaseous samples, as well as a concentration of the compound in a liquid sample, including a solution of solid sample in a solvent.

Accordingly, in some embodiments, the method described herein can be utilized to detect low-volatile explosive, with ultra-low vapor pressure, without concentrating the sample and/or heating the sample prior to contacting it with the device.

Detection of Peroxide-containing Explosives:

The present inventors have devised and successfully practiced a process of depositing metal oxide particles on nanostructures such as SiNWs.

Embodiments of the present invention therefore also relate to a process of generating particles of a metal oxide on a nanostructure. The process is effected by subjecting a metal or an organometallic complex of the metal to atomic layer deposition in the presence of an oxygen source, in the presence of the nanostructure.

The process may be effected while utilizing ALD for seeding metal particles on the nanostructure surface, and generating oxides of the metal particles by means of an oxygen source. Thus, in some embodiments, a nanostructure is contacted with a source of the metal (metal or an organometallic complex of the metal), a source of oxygen (e.g., water), and is subjected to atomic layer deposition procedure. The LAD procedure can be effected for several cycles and the size of the obtained metal oxide particles is determined.

According to embodiments of the present invention, a system is provided for detecting a presence of a peroxide-containing compound, such as a peroxide-containing explosive, as described herein. The system comprises a substrate, such as described herein, and a semiconductor nanostructure (or a plurality of such nanostructures) deposited onto the substrate, as described herein. One or more of the nanostructures has a functional moiety associated therewith (attached thereto), and the functional moiety is configured to interact with a peroxide-containing explosive or compound, such that upon contacting a peroxide-containing explosive with the system, the nanostructure exhibits a detectable change, as described herein, in an electrical property of said nanostructure.

In some embodiments, the electrical property is electrical conductance or electron density, as described herein.

In some embodiments, the system comprises several sensing devices, each comprising differently-modified nanostructures, at least some of the nanostructures have attached thereto a functional moiety for generating a detectable signal upon interacting with a peroxide-containing explosive, and optionally and preferably, at least two sensing devices comprise nanostructures having different such functional moieties, according to any one of the embodiments described herein.

The system may be operated as described in any one of the embodiments described herein for determining a presence of a peroxide-containing explosive in a sample, upon contacting the sample with the system, and determining the change in the electrical property and/or processing the signal generated thereby.

The system may be used also for identifying the peroxide-containing explosive and/or for identifying a presence or absence of a peroxide-containing explosive (e.g., determining if a peroxide-containing compound is an explosive or a non-explosive, chemically-related compound), as described herein.

In some of any one of these embodiments, the functional moiety comprises particles of a metal oxide, as described herein, which can be attached to the nanostructure by atomic layer deposition, as described herein.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The following abbreviations are used herein to define fractions of amounts:

ppth=parts per thousand
ppm=parts per million ppb=parts per billion
ppt=parts per trillion
ppq=parts per quadrillion As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "aminoalkyl" is used herein to describe an alkyl substituted by an amine, as defined herein. In some embodiments, the amine substitutes a terminal carbon atom in the alkyl.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')— group in cases where the amine-oxime is an end group, as this phrase is defined hereinabove.

The term "halide" and "halo" describes fluorine, chlorine, bromine or iodine. The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

The term "silyl" describes a —SiR'R"R'" end group or a —SiR'R"— linking group, as these phrases are defined hereinabove, whereby each of R', R" and R'" are as defined herein.

The term "siloxy" describes a —Si(OR')R"R'" end group or a —Si(OR')R"— linking group, as these phrases are defined hereinabove, whereby each of R', R" and R'" are as defined herein.

The term "silaza" describes a —Si(NR'R")R'" end group or a —Si(NR'R")— linking group, as these phrases are defined hereinabove, whereby each of R', R" and R'" is as defined herein.

The term "silicate" describes a —O—Si(OR')(OR")(OR'") end group or a —O—Si(OR')(OR")— linking group, as these phrases are defined hereinabove, with R', R" and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

As used herein, the term "methyleneamine" describes an —NR'—CH$_2$—CH=CR"R'" end group or a —NR'—CH$_2$—CH=CR"— linking group, as these phrases are defined hereinabove, where R', R" and R'" are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

General:

The detection and identification limits of five types of nitro-containing explosives, (TNT, RDX, HMX, PETN, NG), and some common inteferents (e.g.: musks, Nitrate ions), at ultra-low concentration levels, using variously modified Si nanostructures was tested in an exemplary sensing device (or system).

The building block of the sensing device is a Field Effect Transistor based Silicon Nano-Wire (SiNWs_FET). P-Doped SiNW serve as the main building block and serve as a transistor channel between two electrodes source and drain—and governed by a fluid gate electrode to create a depletion-mode FET which do have a conductive channel when applying a zero gate voltage. The conductivity response to a changing Vg bias scan is a known characteristically as "gateability".

Properly allocated, densely packed and well aligned, arrays of SiNW-FETs are formed. Each array is modified with surface active silanes. Alternating the flow between analyte and analyte free solutions provides the kinetics of association and dissociation of the analyte with the sensing surface. Each analyte interacts with any modified surface differently and its set of kinetics map it one to one.

During one measurement cycle, constant Vg and $V_{SD}$ are applied, while control and analyte alternate and source-drain current ($I_{SD}$) is taken. The height of transient response of the analyte with the surface of the channel reflects its concentration.

When Vg is constant a change in conductivity happens in accordance with a capacitance change of the SiNWs' surface. This happens when rich- or poor-electrons bearing molecules adsorb or leave the surface of the device. This characteristic enables the detection of molecules and dramatically increases the observation levels as compared with other modern detection techniques. This feature enables to exclusively detect explosives and biological samples at ultra-low concentrations (typically ppq to ppt levels).

During measurements, Vg as well as $V_{SD}$ are applied, and the resulting source-drain current ($I_{SD}$) is measured. The current runs through chemically modified silicon nano-wires (Si-NWs) between the electrodes and depends on the chemical and electronic environment of the NWs (AKA FET). When target molecules in the solution attach to the doped NWs, a change occurs in their conductance—resulting in a change in the measured current and indicating the detection of the target molecule.

In typical measurements, the constant voltage between the source and the drain electrodes ($V_{SD}$) was +0.1V, whereas the constant Gate voltage (Vg) was applied in the potentials range of −0.1V to +0.1V (e.g., Vg=+0.1, 0 or −0.1 V); and the resulting current ($I_{SD}$) was measured.

Materials:

All silanes were purchased from Gelest Inc. (Morrisville. Pa.).

The following silanes were used: APTES (Aminopropyltriethoxysilane), en-APTAS (N-(2-aminoethyl)-3-aminopropyltrimethoxysilane), t-Bu (4-amino-3,3-dimethyl butyl triethoxysilane), p-APhS (p-aminophenyltrimethoxysilane), m-APhS (m-A aminophenyltrimethoxysilane) and APDMS (Aminopropyldimethylmethoxysilane). See, FIGS. 1A and 1B.

The following explosives were tested:

TNT (Trinitrotoluene), RDX (Cyclotrimethylenetrinitramine), HMX (Octahydro-1,3,5,7-tetranitro-1,3,5,7-tetrazocine), PETN (Pentaerythritol tetranitrate), 1-NG (1-Nitroglycerin) and nitrate ions ($NO_3^-$). See, FIGS. 1C and 1D.

TNT, RDX, HMX, PETN and NG were acquired from AccuStandard (New Haven Conn.).

TNT, RDX, HMX and PETN were received in standard solutions of 1 ppth (parts per thousand) in methanol-acetonitrile. Nitroglycerin (NG) was neat.

All explosives were diluted to solutions in the range of 1 ppq-100 ppt.

$NH_4NO_3$ and $KNO_3$ were bought from Sigma-Aldrich, and were diluted in 0.1% DMSO in DIW (Deionized water). The nitrate ions were used at the concentrations range of 1 ppb-1 ppm.

Explosives samples were obtained by collecting air-samples of explosive-containing solid sources, at room-temperature, on filter supports (passively or by short sampling pulses of 2-3 seconds). Alternatively, calibrated standard solutions containing known concentrations of the respective explosives were prepared and flowed into the sensing device.

All other chemicals were purchased from Sigma-Aldrich and used as received without further purification, unless otherwise indicated.

Dimethyl Zinc and titanium isopropoxide precursors for ALD decoration of nanowire devices were purchased from Sigma-Aldrich and used as received.

Experimental Procedures:

SiNWs Growth:

Silicon nanowires (SiNWs) were grown as previously described, with final diameter of 20 nm and final length of 2-5 microns. Nanowires were doped in-situ with diborane, leading to 1:4000 (B:Si ratio) p-type nanowire elements.

Three-inch 600 nm thermal oxide Si wafers were cleaned by washing in acetone, isopropyl alcohol (IPA) (5 minutes period each), rinsed with DIW, incubated in hot Piranha for 5 minutes, and then thoroughly rinsed with DIW, and dried by flow of dry $N_2$. The last cleaning step was treatment by oxygen plasma (100 W, 50 sccm of $O_2$ for 200 sec).

Nanowire-Based FETs Array Fabrication:

SiNW Filed Effect Transistors (FETs) were fabricated by standard photolithography procedures. Briefly, passivated source and drain electrodes were deposited by the use of a multilayer resist structure consisting of 300 nm LOR-5A copolymer and 500 nm S-1805 photoresist (purchased from MicroChem Corp.). After exposure and development of the electrode pattern, the contacts were metallized by e-beam evaporation of Ti/Pd/Ti (5/60/10 nm) respectively, and were then passivated from the electrolyte with an insulating layer of $Si_3N_4$ (50 nm-thick) deposited by Inductively Coupled Plasma Enhanced Chemical Vapor Deposition (ICP-PECVD). The separation between the source and drain electrodes, channel length, for each FET was 3 μm (FIG. 5B).

Defining Active Areas (i.e., Wells) Using Photolithography with SU-8 photoresist:

A negative photoresist (SU-8 2000.5) was deposited onto the wafer by spinning at 500 rpm for 10 seconds then 3000 rpm for 30 seconds to obtain a layer thickness of about 500 nm), followed by pre-baking at 95° C. on a hotplate for 1 minute. Wells layer was defined by photolithography (wavelength 350-430 nm, exposure time 7 seconds), using a lithography mask as shown, for example, in FIG. 5A. Then the wafer was post baked at 95° C. for 1 minute, on a hotplate. Development was achieved by using SU-8 developer for 1 minute, and a subsequent wash with isopropyl alcohol (IPA) for 10 seconds, and drying with $N_2$. The wafer was hard baked at 150° C. on a hotplate for 15 minutes.

Electrical Characterization:

Each one of the FET devices was tested in order to identify the suitable nano-devices, using a manual probe station. The NW current ($I_{SD}$) versus time was plotted while scanning Vg (from −0.3V to +0.3V and scan speed of 50 mV/sec) for a given value of $V_{SD}$ (typically 0.1 V). These curves were used for extraction of transconductance values for each device within the array.

Surface Modification by a Stationary Method:

The multiplex SiNWs chip was modified with various derivatives of aminosilanes and non-amine containing silanes.

The surface modification procedure for all silane derivatives was as follows:

The chip was washed with acetone, isopropanol and dried with $N_2$, and was thereafter cleaned with oxygen plasma 500 W 50 sccm for 3 minutes, and washed again with acetone, isopropanol nd dried with $N_2$. The treated chip was heated on a hotplate for 1 hour at 115° C. 1% solutions of each silane derivative were prepared as follows: a solution of 1% of silane derivative in a mixture of 95:5 ethanol:water, was prepared, pH was adjusted to pH=5.0 with acetic acid, and the solution was incubated for 20 minutes at room temperature, and then filtered through 0.2μ. filter and applied to the chip. The covered chip was incubated for 60 minutes, and was thereafter washed with ethanol, dried with $N_2$ and heated at 115° C. for 2 hours.

Multiplex Modification Method by a Flow-Through System:

The microfluidic system was fabricated from polydimethylsiloxane (PDMS). The PDMS was cured overnight in an oven at 60° C. and then cut into rectangular pieces. Each piece was shaped into an eight channel form to enable modification by a multiplex feeding system (a syringe pump with eight outlets). The PDMS was plasma treated (30 W, 50 sccm $O_2$, 3 minutes) and placed over a chip, and the resulting chip was cleaned as described hereinabove. Then, a solution of 95:5 ethanol:$H_2O$, adjusted to pH=5.0 with acetic acid, was flowed until the flow steadied and hereafter different surface modification solutions of silane derivatives, as described hereinabove, were flowed in parallel at 3 μl/minute flow for 1 hour. Thereafter, ethanol was flowed at 20 μl/minutes for 15 minutes, followed by air flow for 30 minutes. The PDMS was removed and the chip was blown dry with $N_2$ and was heated on a hot plate at 115° C. for 2 hours. Exemplary such systems are shown in FIGS. 5C and 5D.

Decoration of SiNW by ZnO Nanoparticles:

Area-dedicated sensing regions are created on a multiplex chip by the ALD-assisted decoration of ZnO nanoparticles of Si nanoFETs, followed by resist removal to lay bare other sub-regions, to be in turn, chemically-modified selectively with silane derivative receptors, as described hereinabove.

ZnO seeding over the nanowires was performed using diethyl zinc and high purity water as the zinc and oxygen sources and nitrogen (99.99%) as a carrier gas. Seeding was effected at a temperature of 70 or 80° C. at a vacuum of $10^{-2}$ Torr. Each precursor was applied during about 0.015 seconds, with a time interval of about 5 seconds. Ten growth cycles were performed.

The same ALD-based process can be readily applied for the decoration of nanowire sensing elements with other metal oxide particles such as, for example, $TiO_2$ and $In_2O_3$ nanoparticles, using appropriate metal precursors.

Sensing Measurements: Electrical properties of the device in a top gated FET as a function of the surface interface were determined for the whole chip, mounted on a PCB substrate enabling its electrical interrogation by the sensing measuring unit.

Usually, the Vg is swept to modulate the carrier concentration in the channel while the $I_{SD}$ is measured while maintaining a constant source-drain voltage ($V_{DS}$=+0.1V).

A microfluidic PDMS enables steady laminar flow in the range of 20 to 5000 μl/minute, using a syringe pump that enables infusion or withdrawal functions.

The conductance (G) of the SiNW-FETs of all devices under test (DUT) is measured using source voltage/measure current method, for obtaining high impedance devices. Such a method quickly charges the stray capacitance of the device under test and rapidly settles to the final output. Usually, the bias between the source and the drain electrodes ($V_{SD}$) is maintained at +0.1V while the fluid gate voltage (Vg) is −0.1V, 0V, +0.1V.

Data Processing:

The raw data obtained is the conductivity G, defined as $dI_{SD}/dV_{SD}$ of all active devices that were connected by wire-bonding. The following algorithm with was used to process the data.

Perform a normalization procedure that reduces variation. This was accomplished by dividing the variation in the response of each device ΔG by its gate response $dI_{SD}/dV_G$ [Fumiaki N. Ishikawa, Marco Curreli, Hsiao-Kang Chang, Po-Chiang Chen, Rui Zhang, Richard J. Cote, Mark E. Thompson, and Chongwu Zhou, A Calibration Method for Nanowire Biosensors to Suppress Device-to-DeviceVariation, ACS Nano, VOL. 3, NO. 12, 3969-3976, 2009].

Employ a mathematical transform, such as, but not limited to, Daubechies wavelets, to filter out signals that do not fit a predetermined functional dependence (an approximate piecewise-linear shape, in the present examples). This operation provided a rough estimate for the onset of the reactions (adsorption and desorption) and for the kinetic magnitudes, particularly the timings of the adsorption and desorption.

Use the times estimates to fit the kinetic features to a predetermined functional dependence. In the present Example, a multi-resolution piecewise-linear regression was used. The linear dependence was geometrically represented by the signal's slope immediately after its transition from non-linear time-dependence to an approximately linear time-dependence.

Integrate the fitted kinetic features into a global estimate of the functional dependence between v1 and v2, where v1 and v2 are the adsorption and desorption rate constants, respectively. In the present example, a linear dependence between v1 and v2 was used. The dependence was estimated by calculating the slope of a straight line in the v1-v2 plane obtained by regression, taking into account all accumulated v1, v2 pairs. The regression non-dimensional quality parameter R-square served as a measure for the inner coherence of the whole process, in the sense that selection parameters were optimized using R-square as a target function. Thus, a feedback system between the above operations (mathematical transform, fitting, integration) was obtained.

Match the obtained explosive fingerprint pattern generated by the given ensemble to a library of previously calculated responses. It was found by the present inventors that such comparison allows to identify the explosive.

XPS Measurements:

XPS studies were performed on SiNWs substrate, using 5600 Multi-Technique System (PHI, USA) with a base pressure of 2.5×10-10 Torr. Samples were irradiated with an Al Kα monochromated source (1486.6 eV) and the outcoming electrons were analyzed by a Spherical Capacitor Analyzer using a slit aperture of 0.8 mm Sample charging was compensated (if required) with a charge neutralizer (C1s at 285 eV was taken as an energy reference). The SAM samples were analyzed at a shallow take-off angle of 23 deg. High-resolution XPS measurements were taken at pass energy of 11.75 eV with 0.05 eV/step interval. SiNWs wafers with 600 nm thermal oxide, SSP prime grade, were cut for the XPS studies to 5×5 $mm^2$ pieces. Prior to the chemical modification, samples were cleaned by an oxygen plasma step, and dehydration on a hot plate for 1-2 hours. The different modifications steps were done as described above in the surface functionalization section.

QCM Measurements:

A home-built QCM analyzer equipped with a Fluke 164T multifunction counter was used for the microgravimetric quartz-crystal-microbalance experiments. Quartz crystals (AT-cut, 9 MHz) sandwiched between two Au electrodes (roughness factor ca. 3.5 with an area of 0.196 $cm^2$) were used in microgravimetric experiments, after deposition of a thin silicon oxide layer of 5 nm by PECVD deposition. Quartz electrodes were cleaned with a piranha solution (70% $H_2SO_4$:30% $H_2O_2$) for 15 minutes, then rinsed thoroughly with DDW (double-distilled water) and dried with a stream of argon before chemical modification steps.

Thickness Measurements by Ellipsometry:

Ellipsometric measurements were carried out on a M-2000DUV Spectroscopic Ellipsometer (J. A. Woollam Co., Inc.). The angles of incidence were 65°, 70° and 75° with a spot size of 2-3 mm. The data were analyzed using WVASE32™ software installed with the ellipsometer. The film thicknesses of the examined layers were calculated by using the Cauchy model.

TEM Measurements:

TEM measurements were performed using Philips Tecnai F20 FES instrument.

Example 1

In initial experiments, a p-doped SiNW FET as described hereinabove was assembled, with a set of six differently modified SiNWs. Modification was achieved using the stationary modification, as described herein.

It is shown herein that various substances can be detected and chemically identified, using the kinetics of binding and unbinding of 5 different explosives. The kinetic measurements were done as follows: A time domain conductance was obtained while alternating between control and analyte. The initial slopes are confined to the first 10-20 seconds intervals of the binding and unbinding reactions that occur between soluble explosives and the Si-NWs-modified receptors (see, FIG. 2).

After each explosives-detectable injection and after each rinse, the initial slopes of $I_{SD}$ as a function of time curves indicate the binding (v1) and unbinding (v2) of the explosives, respectively. Since each type of amino-silane modified nanostructures (e.g., nanowires) has different chemical, steric and electronic characteristics, different $I_{SD}$-time values are obtained for the same explosive with each of the differently modified SiNWs.

Upon measuring v1 and v2, the kinetic factors of each of the 6 modified-SiNW tested, with each of the 6 different explosives were calculated. Notably, the kinetic factors only slightly depend on the concentrations and flow speeds of the solutions.

FIGS. 3A-C exemplify the practiced methodology with APTES-modified SiNW and TNT as the explosive. The kinetic ratio in this example is 0.9358, which is in a great accordance to the value of 0.9871±0.1428, as depicted from Tables 2 and 3.

The kinetic data is summarized in Tables 2 and 3 and is graphically presented in FIG. 4. Clear fingerprints are shown for different explosives and different silanes.

These results are indicative for a successful use of a chip divided into several different subareas—each area (array) comprises modified SiNWs with a different aminosilane derivative. Such a chip can be used not only for the detection but also for the identification of explosives.

nanosensor devices were electrically characterized and normalized by their respective transconductance values, thus minimizing the device-to-device signal variability [shikawa, F. N. et al. ACS nano 3, 3969-3976 (2009)].

Using SiNWs as the sensing elements, various selected surface-bound electron-rich aminosilane derivatives chemically pair with the explosive molecules in a sample, by charge-transfer (i.e. Meisenheimer complexes) and additional chemical interactions [Terrier, F. Chem. Rev. 82, 77-152 (1982)], thus leading to the formation of charges or surface dipole alteration, in close vicinity to the sensing surfaces. Since the analyte molecules are not of biological nature, salt-free baseline solution is used (0.1% DMSO in $H_2O$) in the sensing process, enabling electrolyte screening-free conditions, resulting in a large Debye length (about 1 μm) that confers extremely high sensitivity.

A multiplexed high-throughput detection and identification of explosives by a single chip was achieved by the above-described system.

Surface Modification Characterization:

Up to eight different surface-confined functional groups (receptors), molecules 1 to 8 (FIGS. 1A, 1B and 6), were

TABLE 2

(values of the kinetic ratio (v1 divided by v2))

| Silane | Silanes Abbreviations | TNT | HMX | RDX | PETN | NG |
|---|---|---|---|---|---|---|
| Aminopropyltriethoxysilane | APTES | 1.0131 | 0.4755 | 0.5656 | 1.5223 | 0.5217 |
| N-(2-aminoethyl)-3-aminopropyltrimethoxysilane | en-APTAS | 0.5455 | 1.1217 | 1.1463 | 1.6767 | 0.4849 |
| 4-amino-3,3-dimethyl butyl triethoxysilane | t-Bu | 2.1017 | 0.4831 | 0.7787 | 0.5412 | NA |
| p-aminophenyltrimethoxysilabne | p-APhS | 1.8699 | 1.8839 | 1.7409 | 1.0622 | NA |
| m-aminophenyltrimethoxysilabne | m-APhS | ∞ | 0.4504 | 0.3628 | 0.6533 | 0.2812 |
| Aminopropyldimethylmethoxysilane | APIDMS | 0.8130 | 0.4831 | 0.6411 | 0.4219 | NA |
| Aminoundecanyltriethoxysilane | C11-NH2 | 0 | | | | |

TABLE 3

(standard deviation values of the kinetic ratio (v1 divided by v2))

| Silane | Silane Abbreviation | TNT | HMX | RDX | PETN | NG |
|---|---|---|---|---|---|---|
| Aminopropyltriethoxysilane | APTES | 0.1428 | 0.2628 | 0.2664 | 0.2224 | 0.3692 |
| N-(2-aminoethyl)-3-aminopropyltrimethoxysilane | en-APTAS | 0.3491 | 0.1182 | 0.0941 | 0.0933 | 0.4319 |
| 4-amino-3,3-dimethyl butyl triethoxysilane | t-Bu | 0.0622 | 0.3979 | 0.1553 | 0.0756 | N/A |
| p-aminophenyltrimethoxysilabne | p-APhS | 0.0348 | 0.0692 | 0.1274 | 0.1127 | N/A |
| m-aminophenyltrimethoxysilabne | m-APhS | N/A* | N/A* | 0.3598 | 0.2085 | 0.1791 |

*Explosive-receptor couples that were measured only once.

Example 2

SiNW-FETs Multi-Array Assembly

FIG. 6 presents a SiNW-FETs multi-array, eight arrays in total, each array containing 18 nanodevices, each being individually modified by a surface binding agent, and fed with a common integrated microfluidic channel that enables the flow and interaction of all analytes with the modified arrays.

p-Type boron-doped silicon NWs (p-type SiNW) were grown by CVD, followed by dry-transferring to their destined locations on chip, and the formation of electrical contacts by common lithography and metal depositing steps [Engel, Y. et al. Angew. Chem. Int. Ed. 49, 6830-6835 (2010); Fan, Z. et al. Nano Lett. 8, 20-25, doi:10.1021/nl071626r (2007); Patolsky, F., Zheng, G. & Lieber, C. M. Nature Protocols 1, 1711-1724 (2006)]. The resulting 144 nanosensor devices were electrically characterized and normalized by their respective transconductance values, thus minimizing the device-to-device signal variability selectively anchored to separate portions of the nanowires (separate array spots in a chip) by the use of area-selected silane-coupling procedures [Plueddemann, E. P. Silane coupling agents. (Springer, 1982); He, T. et al. J. Am. Chem. Soc. 128, 14537-14541 (2006); Metwalli, E. et al. J. Colloid Interface Sci. 298, 825-831 (2006)].

The selected silane derivatives (FIGS. 1A, 1B and 6) consist of primary amines (APTES 1, t-Bu, APDMES 6), secondary amines (en-APTAS 3), aromatic amines (aniline derivatives m-APhS 7 and p-APhS 5), as well as amine-free silane derivatives (OTS 2, fluorosilane 4 derivatives), serving as control explosives-non-binding compounds. Clearly, each type of amino-silane modifier has different chemical, steric and electronic characteristics.

A successful modification was characterized by XPS measurements (data not shown).

The surface coverage of the different silane derivatives was measured by means of QCM (quartz crystal microbalance) measurements, and depends on the chemical nature of the silane derivative molecule. Polar silane derivatives display lower surface coverage, in the order of about $3-6\times10^{13}$ molecules/cm$^2$, while non-polar derivatives display higher surface coverage of about $1-4\times10^{14}$ molecules/cm$^2$.

The silane layers were demonstrated to be highly stable for periods of weeks of continuous operation under our experimental conditions.

The devices are real-time sensors, and quickly regenerate after each sensing cycle by flushing a short washing solution pulse that restores the devices to their initial baseline. Hundreds of sensing cycles can be performed using a single sensing platform, for periods of weeks, without considerable degradation of the detection performance.

System Operation and Detection:

Generally, the interaction of electron-deficient nitro-containing explosives with amine groups of silane receptor molecules leads to the formation of surface-confined charges [Buncel, E. & Webb, J. Can. J. Chem. 50, 129-131 (1972); Foster, R. & Fyfe, C. Tetrahedron 22, 1831-1842 (1966)], resulting in the consequent alteration of the nanodevices electrical response. During the measurements, gating was done at the sub-threshold regime that confers higher sensitivity [Yang, X. et ai., Nanotechnology, IEEE Transactions on 11, 501-512 (2012)], and the applied $V_{SD}$ bias allowed operation at a particular region of the device's transconductance.

The resulting source-drain current ($I_{SD}$) that flows through the chemically-modified nanowires is a function of their chemical and electronic environment. Thus, when target molecules in a sample contacts to the nanowires' surface, a change occurs in their conductance—resulting in a change in the measured current and indicating the detection of the target molecule.

FIG. 7A displays the electrical shifts observed upon the interaction of several arrays (portions of nanowires) on a single chip, modified with the amine-containing receptor APTES (1), with TNT-containing samples.

FIG. 7B presents the calibrated responses of the arrays to the analyte ($\Delta I_{sd}$), when normalized by their respective transconductance values (device transconductance ($G_M=dI_{DS}/dV_G$)). As shown in FIG. 7C, this results in relatively small array-to-array variability, even for originally largely dissimilar arrays [shikawa, F. N. et al. ACS nano 3, 3969-3976 (2009)]. As shown in FIG. 7D, all arrays modified with silane derivative (1) also show considerable electrical shifts upon their interaction with different explosive species: TNT (1,3,5 Triacetone triperoxide), RDX (1,3,5-Trinitroperhydro-1,3,5-triazine), HMX (Octahydo-1,3,5,7-tetranitro-1,3,5,7-tetrazocine) and PETN ([3-Nitroxy-2,2-bis(nitromethyl) propyl]nitrate, as well as upon their interaction with non-explosive interferents (e.g: Nitrate, Musk ketone, Musk moskene; data not shown).

Although the interaction with the highly electron-deficient TNT molecules leads to the largest measured electrical shifts, with detection limits down to the ppq (parts-per-quadrillion) concentration range, these results show the low capability to selectively detect different explosive species by nultiarrays chemically-modified with a single functional moiety, as previously reported.

Hence, a selective detection of explosives, and their discriminative identification, based on the real-time mathematical analysis of their interaction, both kinetically and thermodynamically, with a single chip comprising multiple arrays, each bearing different surface functional moiety, has been performed.

To this end, a broad library of amino-silane derivatives was tested for their interaction with multiple explosive species of relevance.

The multi-array chip, with integrated multichannel microfluidics, allows for the simultaneous chemical modification of multiple surface functional moieties, as shown in FIGS. 5C and 5D. Generally, 1% ethanolic solutions of each silane derivative were simultaneously and separately flowed along their respective wells, by means of individual inlet and outlet ports, followed by washing the unbound silanes excess prior to the final curing step, as described hereinabove.

Using such multi-array, each explosive species is expected to exhibit a distinctive pattern of interaction, both kinetically and thermodynamically, with the combinatorial chemically-modified multiarray.

Mathematical Analysis:

Two parameters inherent to the interaction between any explosive chemical species and the surface-confined functional moieties were selected: (1) the signal amplitude, or electrical shift, measured after reaching the asymptotic saturation value of the multi-array device ($I_{SD}$ after equilibrium is achieved) at any concentration of the given explosive, when the $\Delta I_{SD}$ was calibrated by its gate dependence, the transconductance value (Gm), and (2) the initial rates of association and dissociation, measured after the interaction of the multi-array device with a certain explosive species, and the sequential flushing of the sensors surface with a clean baseline solution leading to the unbinding of the explosive species, $V_1$ and $V_2$ respectively (see, FIG. 8C).

To achieve this goal, a five-tier algorithm was developed, able to extract, and analyze, in real time all the above mentioned parameters, followed by the final identification of the molecular species under test based on a formerly built fingerprints database (see, FIG. 8E).

The Signal processing algorithm steps are presented in FIGS. 8A-E.

Raw response (FIG. 8A) followed by calibrating each array's absolute raw response against its gate dependence $dI_{SD}/dV_G$ (FIG. 8B). Mathematically extracting the kinetic ratio (v1/v2) and the calibrated absolute response under steady state conditions (FIG. 8C). The statistical dependence of the kinetic constants was estimated by the slope of a straight line in the v1-v2 plane obtained by regression using R-square as a target function, taking into account all accumulated v1-v2 pairs (FIG. 8D). Chemical identification wherein a matching is done between the pattern generated by the given ensemble response to a library of previously calculated responses (FIG. 8E).

Steady-State Multiplex Analysis:

FIGS. 9A-D display the results obtained from the interaction of several common explosives with a multi-array of nanowires differently-modified with various silane derivatives (1, 2, 3, and 5 of FIG. 6), and present the interaction of each explosive species, in terms of $\Delta I_{SD}/G_M$ values measured under steady state conditions (constant analyte concentration under constant flow) with various functional moieties of the combinatorial multi-array.

As shown therein, different explosives species display a distinctive pattern of interaction with the multi-array, thus allowing for a simple and straightforward identification of the molecule under test. As further shown therein, at a steady state, the calibrated absolute response of different silanes to a certain explosive species is differential, such that their relative responses create a concentration independent pattern to make an explosive's unique fingerprint. The interaction pattern of each explosive species is kept constant regardless its concentration in the tested sample.

This distinctive fingerprinting pattern of interaction is common to all arrays within a single multi-array device, and across different multi-array devices (chips) (n>50 chips).

Furthermore, control unmodified nanodevices on the same chip, as well as devices modified with non-amino silanes (e.g. alkyl or fluoroalkyl silanes) do not produce any observable signal upon interacting with even relatively high concentrations of explosives (in the µM range: ppm levels) (data not shown).

These data demonstrate the suitability of moieties containing electron-donating groups, e.g. amine, thiol and calyx[4]pyrrole groups, for the binding interaction of electron deficient explosive species to the nanowires surface.

Multiplex Analysis of Kinetic Parameters:

Kinetic parameters inherent to the chemical interaction between different explosives species and the combinatorially-modified nanosensors array were employed to enhance the selectivity of the sensing process, and the accurate identification of the molecular species under test.

After each explosive binds and unbinds, the initial slopes of $I_{SD}$ as a function of time curves indicate the binding (v1) and unbinding (v2) processes, respectively. After measuring, v1 and v2, the kinetic factors of 6 silanes, each one of them for 5 different explosives, were calculated.

Multiple explosive species were tested against the silanes derivatives-combinatorially modified multi-array. The kinetic data is summarized in FIGS. 10A-F. As shown therein, a unique fingerprint pattern that enables the discrimination of all tested explosives was created by these measurements (see 'radar plot' two-dimensional presentation on the right panel). The whole set of mathematically-derived kinetics produces a profile library (left panel, bar graph), where each result is calculated over >50 experiments performed with at least 5 different chips.

As further shown therein, every silane-to-explosive couple has its own and unique kinetic v1/v2 ratio, creating together a kinetic data matrix. Thus, the algorithm-derived kinetic ratios of the real-time measured transient electrical signals (v1/v2) map in a one to one way.

This matrix is actually a library—or "fingerprint"—of each one of the explosives under measurement, which can be readily expanded by similarly measuring additional materials (both explosives and functional moieties) and utilized in the detection and identification of novel types of explosives.

As noted, measurements of the kinetics complex ratios of any given explosive species with the combinatorially-modified multi-array do not show a concentration-dependence behavior (in the range of 1 ppq-1 ppb), nor a flow rate dependency, but are only affected by the nature of the explosive-to-receptor (functional group) pair tested.

It is to be further noted that potential interfering molecules give rise to different interaction patterns with the combinatorial chemically-modified multi-array, and can be easily discriminated in real-time from known explosive molecules of interest. Additionally, by virtue of the algorithm used and the combinatorial nature of the sensing array, detecting and identifying explosives mixtures is also enabled.

Example 3

A directly and sensitive detection and identification of peroxide-based explosives, such as Triacetone trioxide (TATP) and hexamethylene triperoxide diamine (HMDT), infamous for their clandestine production due to the availability of the ingredients and the ease of production, has also been demonstrated.

Conventional explosives sensors rely on the presence of nitro groups. Unlike conventional nitro-containing explosives, TATP displays a significant vapor pressure at ambient temperature (6.95 Pa at 25° C.), but since it does not contain nitro groups, its detection poses a serious challenge [Oxley et al. *Propellants, Explosives, Pyrotechnics* 34, 539-543 (2009); Önnerud, H., Wallin, S. & Östmark, H. in *Intelligence and Security Informatics Conference (EISIC)*, 2011 European. 238-243 (IEEE)]. HMTD further exacerbates this limitation by displaying an extremely low vapor pressure. Thus, the development of novel approaches for the sensitive and rapid detection of these hazardous molecules is of great importance in the field of homeland security.

As shown in FIG. 11, peroxide-based explosives did not show any appreciable interaction with the combinatorially-modified multi-array, modified with silane derivatives (shown in FIG. 6), even at the highest tested concentrations of ppm (part-per-millions).

Thus, a methodology for the area-selected decoration of nanowire devices with ZnO (or other metal oxide) nanoparticles, by a low-temperature ALD (atomic layer deposition) process, was developed [Devika et al. *ChemPhysChem* 11, 809-814 (2010)]. FIG. 20A presents schematically this methodology, effected by area-selected decoration of ZnO NPs by an additional photolithography masking step, before the subsequent chemical modification of the undecorated array areas, with the silane-derivatives.

The decoration process leads to the formation of a dense layer of ZnO NPs on the NWs sensing elements, with the capability of controlling over the nanoparticles dimensions, which typically range between 4-10 nm. FIG. 20B shows a representative TEM image of ALD-deposited nanoparticles (70° C., 10 cycles) decorating p-type SiNWs (of about 20 nm diameter).

The deposited metal oxide nanoparticles serve as a basis for the complexation and further detection of peroxide-containing explosives.

As shown in FIG. 21, the surface-decorated metal oxide nanoparticles were shown as effective complexation centers for the binding and detection of TATP and HMDT. FIG. 21 presents the interaction of ZnO NPs-decorated nanowires in the presence of TATP (triacetone triperoxide), HMTD (Hexamethylene triperoxidediamine), TNT, RDX, PETN and HMX. As further shown therein, besides peroxide-based molecules, ZnO complex with the six-membered rings of TNT and RDX, yet is inert to the eight-membered ring of HMX and the linear structured nitro-carrying explosives (PETN, NG). The n-type ZnO is known to donate electrons to $H_2O_2$ but hydrogen peroxide is detected only at 250 ppm. Irrespective of their concentration, all explosives are discriminated through their respective kinetic ratio.

Overall, it is shown herein that exemplary devices according to some embodiments of the present invention, can sensitively detect TATP and HMTD down to the low ppt concentration range, and effectively discriminate and identify these peroxide-containing explosives against nitro-containing explosives, by the simple use of a single chemically-modified combinatorial platform. As well, a clear discrimination against simple peroxide species, i.e. hydrogen peroxide, can be readily attained.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for identifying an explosive, the system comprising a substrate carrying a plurality of sensing devices, each sensing device comprising at least one semiconductor nanostructure having attached thereto a functional moiety selected to interact with an explosive-containing sample, wherein each sensing device is configured to generate a detectable signal responsively to said interaction, and wherein at least two different sensing devices comprise different functional moieties, and
   a signal processor having a circuit configured to extract, from each generated signal, a kinetic parameter describing a respective interaction of said sample with a respective sensing device, thereby to construct an explosive fingerprint indicative of said explosive, said explosive fingerprint being defined as a set of kinetic parameters, at least one parameter for each sensing device, wherein said kinetic parameter comprises a ratio between a first parameter which is slope describing rise of a respective signal and a second parameter which is a slope describing a descent of said respective signal;
   wherein at least one of said sensing device comprises a plurality of semiconductor nanostructures, and is configured to generate a group of signals, a signal for each of at least a portion of said plurality of nanostructures, and wherein said signal processor is configured to extract said kinetic parameter collectively from said group of signals, and
   wherein said signal processor is configured to extract pairs of parameters from each signal of said group of signals, thereby to provide a plurality of pairs of parameters, and to calculate said kinetic parameter by fitting said plurality of pairs of parameters to a predetermined fitting function.

2. The system according to claim 1, further comprising a data processor configured to access a database of explosive fingerprints, and to search said database for a database fingerprint matching said constructed fingerprint.

3. The system according to claim 1, wherein said fitting function is a linear function characterized by said slope.

4. The system according to claim 1, wherein said signal processor is configured to extract at least one additional parameter from at least one of said signals, and to construct said explosive fingerprint based on said kinetic parameter and based on said at least one additional parameter.

5. The system according to claim 4, wherein said at least one additional parameter describes a plateau segment of said at least one signal.

6. The system of claim 1, wherein at least one kinetic parameter is extracted from a conductance curve of a respective nanostructure as a function of the time.

7. The system of claim 1, wherein a functional moiety in at least one of said sensing devices is a moiety which forms a complex with said explosive.

8. The system of claim 7, wherein a functional moiety in at least one of said sensing devices is independently a moiety that interacts with a nitro-containing explosive by forming a charge transfer complex.

9. The system of claim 8, wherein said functional moiety in at least one of said sensing devices is independently an electron donating moiety.

10. The system of claim 8, wherein a length of said functional moiety in at least one of said sensing devices is smaller than 2 nm.

11. The system of claim 8, wherein said functional moiety in at least one of said sensing devices is independently selected from the group consisting of $C_{1-10}$ alkyl, $C_{1-10}$ alkenyl, aryl and cycloalkyl, each being substituted by an electron donating group.

12. The system of claim 11, wherein said electron donating group is selected from the group consisting of amine, thiol, pyrrole, alkoxy, thioalkoxy, aryloxy and thioaryloxy.

13. The system of claim 11, wherein said electron donating group is amine.

14. The system of claim 8, wherein said functional moiety in at least one of said sensing devices is independently selected from the group consisting of a heteroalicyclic and a heteroaryl, each comprising a heteroatom that functions as an electron donating group.

15. The system of claim 8, wherein said functional moiety in at least one of said sensing devices is independently selected from the group consisting of aminopropyl, N-(2-aminoethyl)-3-aminopropyl, 4-amino-3,3-dimethyl butyl, p-aminophenyl, and m-aminophenyl.

16. The system of claim 7, wherein a functional moiety in at least one of said sensing devices is independently a moiety that interacts with a peroxide-containing explosive.

17. The system of claim 16, wherein said functional moiety that interacts with the peroxide-containing explosive is independently a moiety that comprises particles of a metal oxide.

18. The system of claim 17, wherein said metal oxide is selected from the group consisting of zinc oxide, titanium dioxide, lithium oxide, copper oxide, an oxide of indium, and an oxide of cadmium.

19. The system of claim 1, wherein a functional moiety in at least one of said sensing devices is independently a functional moiety that interacts with a nitro-containing explosive by forming a charge transfer complex, and a functional moiety in at least another one of said sensing devices is independently a functional moiety that comprises particles of a metal oxide.

20. The system of claim 1, wherein said at least one nanostructure comprises nanowires.

21. The system of claim 1, wherein at least one of said at least one semiconductor nanostructure is a semiconductor nanostructure which comprises silicon.

22. The system claim 1, further comprising a detector constructed and arranged to determine changes in an electrical property of said at least one nanostructure.

23. The system of claim 1, wherein at least one sensing device of said sensing devices comprises or is part of a transistor.

24. A method of identifying an explosive in a sample, the method comprising contacting the sample with the system of claim 1, and identifying the explosive in the sample based on said explosive fingerprint.

* * * * *

UNITED STATES PATENT AND TRADEMARK OFFICE
CERTIFICATE OF CORRECTION

PATENT NO. : 10,241,076 B2  
APPLICATION NO. : 14/762001  
DATED : March 26, 2019  
INVENTOR(S) : Fernando Patolsky et al.

Page 1 of 1

It is certified that error appears in the above-identified patent and that said Letters Patent is hereby corrected as shown below:

On the Title Page

Item (73) Assignee:  
"System" should be changed to -- Systems --

Signed and Sealed this  
Second Day of July, 2019

Andrei Iancu  
*Director of the United States Patent and Trademark Office*